United States Patent
Tranter et al.

(10) Patent No.: US 10,933,135 B2
(45) Date of Patent: Mar. 2, 2021

(54) METHODS FOR THE TREATMENT OF CARDIAC HYPERTROPHY

(71) Applicant: UNIVERSITY OF CINCINNATI, Cincinnati, OH (US)

(72) Inventors: Michael Tranter, Cincinnati, OH (US); Sarah Anthony, Cincinnati, OH (US); Samuel Slone, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/090,705

(22) PCT Filed: Apr. 5, 2017

(86) PCT No.: PCT/US2017/026114
§ 371 (c)(1),
(2) Date: Oct. 2, 2018

(87) PCT Pub. No.: WO2017/176866
PCT Pub. Date: Oct. 12, 2017

(65) Prior Publication Data
US 2019/0117772 A1 Apr. 25, 2019

Related U.S. Application Data

(60) Provisional application No. 62/318,752, filed on Apr. 5, 2016, provisional application No. 62/371,444, filed on Aug. 5, 2016.

(51) Int. Cl.
| | | |
|---|---|---|
| *A61K 45/06* | (2006.01) |
| *C12N 15/113* | (2010.01) |
| *A61P 9/00* | (2006.01) |
| *A61K 31/352* | (2006.01) |
| *A61K 31/4025* | (2006.01) |
| *A61K 35/44* | (2015.01) |
| *G01N 33/542* | (2006.01) |
| *A61K 9/00* | (2006.01) |

(52) U.S. Cl.
CPC .......... *A61K 45/06* (2013.01); *A61K 31/352* (2013.01); *A61K 31/4025* (2013.01); *A61K 35/44* (2013.01); *A61P 9/00* (2018.01); *C12N 15/113* (2013.01); *G01N 33/542* (2013.01); *A61K 9/0019* (2013.01); *A61K 9/0053* (2013.01); *C12N 2310/14* (2013.01)

(58) Field of Classification Search
CPC .... A61K 45/06; A61K 35/44; A61K 31/4025; A61K 31/352; A61K 9/0053; C12N 15/113; C12N 2310/14; G01N 33/542; A61P 9/00
See application file for complete search history.

(56) References Cited

PUBLICATIONS

Wu, "Identification and Validation of Novel Small Molecule Disruptors of HuR-mRNA Interaction", ACS Chemical Biology, 2015, 10, pp. 1476-1484.*
Slone, "Activation of Human antigen R (HuR) downstream of p38-MAPK promotes cardiomyocyte hypertrophy through modulation of NFAT activity", The FASEB Journal, Apr. 1, 2016, 30:1_supplement (abstract).*
Extended European Search Report for corresponding EP Application No. 17779734.7 dated Oct. 23, 2019.
Prasanna Krishnamurthy et al, Myocardial knockdown of mRNA-stabilizing protein HuR attenuates post-MI inflammatory response and left ventricular dysfunction in IL-10-null mice; The FASEB Journal Jul. 2010; 24 (8): 2484-2494.
International Search Report & Written Opinion for corresponding PCT/US2017/026114 dated Sep. 1, 2017.
AACR 2016: Abstracts 2697-5293, CTI Meeting Technology, Mar. 28, 2016.
Sahana Suresh Babu et al, "RNA stabilizing proteins as molecular targets in cardiovascular pathologies"; Trends Cardiovasc Med, Aug. 20, 2016.
Anke C. Rosenkranz et al, "Regulation of Human Vascular Protease-Activated Receptor-3 Through mRNA Stabilisation and the Transcription Factor NFAT"; Molecular Pharmacology Fast Forward; Mar. 19, 2011.
S. Slone et al, "Activation of HuR downstream of p38 MAPK promotes cardiomyocyte hypertrophy"; Cell Signal Nov. 2016, 28 (11): 1735-1741.
Michael Tranter et al, "Abstract 60: Cardiac-specific Deletion of HuR Reduces Pathological Hypertrophy and Ventricular Remodeling Following Tranverse Aortic Constriction"; Circulation Research, 2015; 117: A60.
Xiaoqing Wu et al, "Indentification and Validation of Novel Small Molecule Disruptors of HuR-mRNA Interaction"; ACS Chem Biol. Jun. 19, 2015 10 (6); 1476-1484.

* cited by examiner

*Primary Examiner* — Sahar Javanmard
(74) *Attorney, Agent, or Firm* — Dinsmore & Shohl LLP

(57) ABSTRACT

Methods for the treatment of cardiac hypertrophy are described. Additionally, the presently disclosed subject matter relates to the use of small molecule compounds for the inhibition of Human antigen R (HuR)-mRNA interaction, and more particularly for the reduction of nuclear factor of activated T cells (NFAT) transcriptional activity. Novel methods of screening for small molecule compounds for inhibition of RNA binding proteins interaction with their target RNA (such as HuR-mRNA interactions) or for inhibition of DNA binding proteins to their target DNA are also described.

8 Claims, 12 Drawing Sheets
Specification includes a Sequence Listing.

SEQUENCE LISTING

```
<160> NUMBER OF SEQ ID NOS: 7

<210> SEQ ID NO 1
<211> LENGTH: 20
<212> TYPE: DNA
<213> ORGANISM: homo sapiens

<400> SEQUENCE: 1
accacagtcc atgccatcac                                                    20

<210> SEQ ID NO 2
<211> LENGTH: 20
<212> TYPE: DNA
<213> ORGANISM: homo sapiens

<400> SEQUENCE: 2
tccaccaccc tgttgctgta                                                    20

<210> SEQ ID NO 3
<211> LENGTH: 18
<212> TYPE: DNA
<213> ORGANISM: homo sapiens

<400> SEQUENCE: 3
aggagaagat gccggtag                                                      18

<210> SEQ ID NO 4
<211> LENGTH: 18
<212> TYPE: DNA
```

```
<213> ORGANISM: homo sapiens

<400> SEQUENCE: 4
gcttttcaag agggcaga                                              18

<210> SEQ ID NO 5
<211> LENGTH: 23
<212> TYPE: DNA
<213> ORGANISM: homo sapiens

<400> SEQUENCE: 5
gggccaaatt tgaatccctc ttc                                        23

<210> SEQ ID NO 6
<211> LENGTH: 20
<212> TYPE: DNA
<213> ORGANISM: homo sapiens

<400> SEQUENCE: 6
ggagccaggt gtgaacttcc                                            20

<210> SEQ ID NO 7
<211> LENGTH: 54
<212> TYPE: RNA
<213> ORGANISM: homo sapiens

<400> SEQUENCE: 7
gcgaauuggg cccgacgucg cauggcuuuu auuuauuuug cauggccgcg ggau      54
```

METHODS FOR THE TREATMENT OF CARDIAC HYPERTROPHY

CROSS-REFERENCE TO RELATED APPLICATION

This application depends from and claims priority to U.S. Provisional Application Nos. 62/318,752 filed Apr. 5, 2016, and 62/371,444 filed Aug. 5, 2016, the entire contents of which are incorporated herein by reference.

REFERENCE TO SEQUENCE LISTING SUBMITTED ELECTRONICALLY VIA EFS-WEB

The content of the electronically submitted sequence listing (10738-500 Seq Listing_ST25.txt, which is 2 KB and created on Apr. 5, 2016) filed with the application is incorporated herein by reference in its entirety.

TECHNICAL FIELD

The presently disclosed subject matter relates to novel methods for the treatment of cardiac hypertrophy. Additionally, the presently disclosed subject matter relates to the use of small molecule compounds for the inhibition of Human antigen R (HuR)-mRNA interaction, and more particularly for the reduction nuclear factor of activated T cells (NFAT) transcriptional activity. Novel methods of screening for small molecule compounds for inhibition of mRNA binding proteins interaction with their target RNA, such as HuR-mRNA interactions, are also described.

BACKGROUND

Pathological cardiac hypertrophy and associated cardiac conditions remain a global health problem. Cardiac hypertrophy is the enlargement of heart that is activated by both mechanical and hormonal stimuli and enables the heart to adapt to demands for increased cardiac output or to injury. The initial development of cardiac hypertrophy is a beneficial and compensatory response to maintain cardiac output in the face of hemodynamic stress. However, this response is frequently associated with a variety of distinct pathological conditions, such as hypertension, aortic stenosis, myocardial infarction, cardiomyopathy (including hypertrophic cardiomyopathy), valvular regurgitation, cardiac shunt, heart failure (including congestive heart failure), etc. For example, cardiac hypertrophy in response to pathological etiologies such as hypertension or valvular dysfunction is a known driver of heart failure, and some reports have also questioned its necessity as a compensatory development and suggest a benefit to suppressing the initial development of hypertrophy. The treatment of cardiac hypertrophy varies depending on the underlying cardiac disease. However, there is no generally applicable therapy for the treatment of cardiac hypertrophy. Accordingly, there remains a need in the art for novel methods of treating cardiac hypertrophy and associated cardiac conditions, as well as novel assays and methods of screening for small molecule compounds for the treatment of cardiac hypertrophy. Furthermore, there remains a need in the art for novel assays and methods of screening for small molecule compounds that can inhibit the interaction of potential therapeutic target RNA binding proteins and their target RNA.

SUMMARY

Accordingly, the presently disclosed subject matter relates to methods of treating cardiac hypertrophy. Additionally, methods to inhibit HuR in cardiomyocyte cells, and methods to inhibit NFAT in cardiomycte cells are disclosed herein.

One embodiment of the presently-disclosed subject matter is directed to a method of treating cardiac hypertrophy in a subject in need of treatment thereof, the method comprising administering to the subject an effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof.

A further embodiment is directed to a method of inhibiting Human antigen R (HuR) in a cardiomyocyte cell, the method comprising contacting the cell with an effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof.

An additional embodiment is directed to a method of inhibiting nuclear factor of activated T cells (NFAT) transcriptional activity in a cardiomyocyte cell, the method comprising contacting the cell with an effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof.

Another embodiment is directed to a method of inhibiting NFAT transcriptional activity in a subject in need of inhibiting NFAT transcriptional activity, the method comprising administering to the subject an effective amount of a small molecule inhibitor of HuR-mRNA interaction. In embodiments, the inhibitor of HuR-mRNA interaction is KH-3. In some embodiments, the small molecule inhibitor of HuR-mRNA interaction is selected from the group consisting of KH-3, CMLD-1, CMLD-2, or a combination thereof.

In further embodiments, an assay for identifying an agent that modulates the interaction of a RNA binding protein with a target RNA is disclosed. The assay comprises 1) providing a multiplexed localized surface plasmon resonance (LSPR) device biosensing device comprising a plurality of nanoparticle arrays, the device produced by: (a) transferring a desired pattern to a photoresist on a substrate using photolithography; (b) spin coating at least two coats of polymer to form a polymer layer; (c) drop coating a plurality of polystyrene particles of a desired shape and size on the polymer layer; (d) depositing a nanomeric layer of gold; (e) removing the polystyrene particles to create a hole-mask; (f) etching the hole mask to generate a plurality of holes; (g) depositing a metal into the holes; (h) removing the polymer layer and the photoresist to yield a plurality of nanoparticle arrays in a desired pattern; and (i) functionalizing the nanoparticle arrays with target RNA specific to the RNA binding protein; 2) contacting the target RNA with a RNA binding protein that is specific to the target RNA in the absence and in the presence of a candidate of interest which is expected to modulate the interaction of said RNA binding protein with said target RNA for a sufficient period of time so that a complex between said target RNA and said RNA binding protein can be formed; 3) detecting the complex formed in step 2); 4) determining whether there is a decrease in the amount of complex formed between the case of when a candidate compound is preset compared to when the candidate is absent in step 3); and 5) choosing a candidate compound as an inhibitor of interaction of the RNA binding protein with the target RNA where a decrease is determined in step 4).

These and additional aspects and features of the instant invention will be clarified by reference to the figures and detailed description set forth herein.

BRIEF DESCRIPTION OF THE DRAWINGS

FIG. 11A depicts representative shifts observed with addition of DNA, RNA, and HuR protein to the nanoparticle arrays. FIG. 11B shows the quantitative assessment demonstrating reproducibility of the observed LSPR shifts. FIG. 11C demonstrates that the addition of the HuR inhibitor CMLD-1 resulted in a measurable disruption of HuR-RNA binding as evidenced by the observed leftward shift of 10 nm.

DETAILED DESCRIPTION

Figure 1A:
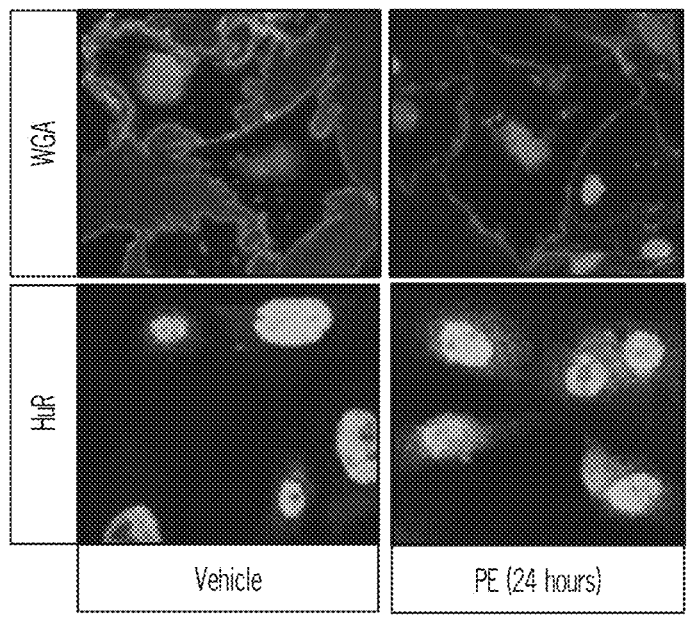
FIG. 1A-C. HuR nucleo-cytoplasmic shuttling correlates with an increase in cell size/hypertrophic growth in neonatal rat ventricular myocytes (NRVMs). Following a 24-hour exposure to PE (10 µM), NRVMs show a significant increase in cell area as indicated by WGA staining (FIG. 1A, top panel) and cytoplasmic translocation of HuR as determined by HuR IHC (FIG. 1A, bottom panel). Cell surface area was quantitatively determined using NIH Image J. and is expressed as fold-increase in area compared to vehicle control treated cells (FIG. 1B). HuR translocation was quantified as the ratio of cytoplasmic to total cell fluorescent intensity. N≥4 for each group (each N represents the average measurement of 10 cells per well). *P≤0.05 vs. Veh control.

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not limited to these preferred aspects.

Unless defined otherwise, all technical and scientific terms used herein have the same meaning as commonly understood by one of ordinary skill in the art to which the presently-disclosed subject matter belongs.

Human antigen R (HuR) is a widely expressed RNA binding protein that interacts with specific AU-rich domains in target mRNAs and exerts post-transcriptional regulation of target mRNA by a number of means, including RNA stability, translation, splicing, polyadenylation, or microRNA targeting. While relatively little is known about the role of HuR in the myocardium, RNA binding proteins such as HuR could potentially serve central regulators of cardiac physiology and pathology (J. Rajasingh, *The many facets of RNA-binding protein HuR*, Trends in Cardiovascular Medicine. (2015) 1-3. doi:10.1016/j.tcm.2015.03.013, and S. S. Babu, D. et al., *RNA-stabilizing proteins as molecular targets in cardiovascular pathologies*, Trends in Cardiovascular Medicine. (2015) 1-8. doi: 10.1016/j.tcm.2015.02.006). For example, recent work by Krishnamurthy et al. suggests that HuR is likely to play a central role in the cardiac response to stress (P. Krishnamurthy et al., *IL-10 Inhibits Inflammation and Attenuates Left Ventricular Remodeling After Myocardial Infarction via Activation of STAT3 and Suppression of HuR*, Circ. Res. 104 (2009) e9-e18. doi:10.1161/CIRCRESAHA.108. 188243, and P. Krishnamurthy, et al., *Myocardial knockdown of mRNA-stabilizing protein HuR attenuates post-MI inflammatory response and left ventricular dysfunction in IL-10-null mice*, The FASEB Journal. 24 (2010) 2484-2494. doi:10.1096/fj.09-149815). They showed that HuR expression increased following ischemic injury and knockdown with shRNA delivered via intramyocardial injection significantly reduced post-infarct remodeling and was accompanied by a decrease in transforming growth factor-β (TGF-β) expression. However, it is unclear from this work whether HuR plays a direct role in cardiac myocytes. Furthermore, this prior work focused on the role of HuR on fibrosis and ventricular remodeling following acute ischemic injury, but its role in the development of cardiac hypertrophy is completely unknown.

The presently disclosed data demonstrates that HuR undergoes cytoplasmic translocation, indicative of its activation, in hypertrophic cardiac myocytes. Specifically, HuR cytoplasmic translocation is significantly increased in NRVMs (neonatal rat ventricular myocytes) following treatment with phenylephrine or angiotensin II, agonists of two independent Gaq-coupled GPCRs known to induce hypertrophy. This Gq-mediated HuR activation is dependent on p38 MAP kinase, but not canonical Gq-PKC signaling. Furthermore, we show that HuR activation is necessary for Gq-mediated hypertrophic growth of NRVMs as siRNA mediated knockdown of HuR inhibits hypertrophy as measured by cell size and expression of ANF (atrial natriuretic factor). Similarly, the administration of pharmacological inhibitors of HuR inhibits Gq-mediated hypertrophic growth of NRVMs as measured by cell size and expression of ANF. Additionally, HuR overexpression is sufficient to induce hypertrophic cell growth. To decipher the downstream mechanisms by which HuR translocation promotes cardiomyocyte hypertrophy, we assessed the role of HuR in the transcriptional activity of NFAT (nuclear factor of activated T cells), the activation of which is a hallmark of cardiac hypertrophy. Using an NFAT-luciferase reporter assay, we show an acute inhibition of NFAT transcriptional activity following pharmacological inhibition of HuR. Further, we show that pharmacological inhibition of HuR reduces ventricular dilation and improves ejection fraction in a pressure overload (aortic constriction) mouse model of heart failure. Pharmacological inhibition of HuR in mice that were subjected to aortic constriction (TAC) to induce cardiac hypertrophy and heart failure showed significantly preserved cardiac structure by preventing further increases in left ventricle end diastolic volume and left ventricle end systolic volume. This result is confirmed by showing that pharmacological inhibition of HuR also blunts further increases in left ventricle (LV) diameter. Additionally, treatment with a pharmacological inhibitor of HuR showed a strong trend toward improving cardiac function (as measured by ejection fraction; following pressure overload-induced pathological cardiac hypertrophy), and there is also a strong trend toward a reduction in cardiac hypertrophy following treatment with a pharmacological inhibitor of HuR (as measured by either heart weight to body weight or heart weight to tibia length ratio). Our results identify HuR as a novel mediator of cardiac hypertrophy downstream of the Gq-p38 MAPK pathway, and suggest modulation of NFAT activity as a potential mechanism. Based on the presently-disclosed data, small molecule inhibitors of HuR-mRNA interaction, including but not limited to KH-3, CMLD-1, CMLD-2, or combinations thereof, may yield favorable therapeutic indices in patients suffering with cardiac hypertrophy and related pathological cardiac conditions such as hypertension, aortic stenosis, myocardial infarction, cardiomyopathy (including hypertrophic cardiomyopathy), valvular regurgitation, cardiac shunt, and heart failure (including congestive heart failure).

Accordingly, the presently-disclosed subject matter includes a method of treating cardiac hypertrophy in a subject in need of treatment thereof, the method comprising administering to the subject an effective amount of a small molecule inhibitor of HuR-mRNA interaction. In embodiments, the small molecule inhibitor of HuR-mRNA interaction is KH-3. "KH3" is a small molecule inhibitor of HuR-mRNA interaction and is available from Professor Liang Wu in the Department of Molecular Biosciences, University of Kansas, Lawrence, Kans. 66045, United States). In some embodiments, the small molecule inhibitor of HuR-mRNA interaction is selected from the group consisting of KH-3, CMLD-1, CMLD-2, or a combination thereof. CMLD-" is a small molecule inhibitor of HuR-mRNA interaction having the following chemical structure:

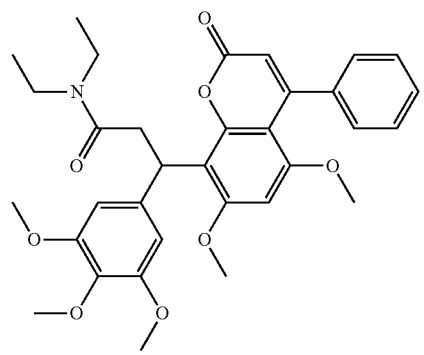 [SMILES: CCN(CC)C(=O)CC(c1cc(OC)c(OC)c(OC)c1)c1c(OC)cc(OC)c2c(-c3ccccc3)cc(=O)oc12]

CMLD-2 is a small molecule inhibitor of HuR-mRNA interaction having the following chemical structure:

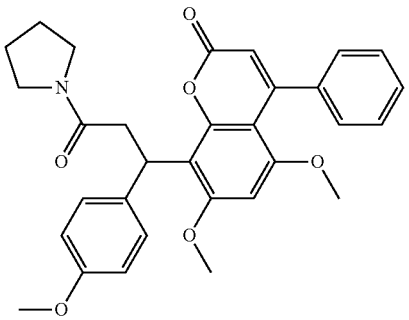 [SMILES: COc1ccc(C(CC(=O)N2CCCC2)c2c(OC)cc(OC)c3c(-c4ccccc4)cc(=O)oc23)cc1]

Cardiac hypertrophy is the enlargement of heart that is activated by both mechanical and hormonal stimuli and enables the heart to adapt to demands for increased cardiac output or to injury. Adult myocyte hypertrophy is initially beneficial as a short term response to impaired cardiac function by permitting a decrease in the load on individual muscle fibers, thus allowing for maintained cardiac output in the face of hemodynamic stress. With severe, long-standing overload, however, the hypertrophied cells begin to deteriorate and die. This response is frequently associated with a variety of distinct pathological conditions, such as hypertension, aortic stenosis, myocardial infarction, cardiomyopathy, valvular regurgitation, cardiac shunt, congestive heart failure, and other pathological conditions. The enlargement of embryonic heart is largely dependent on an increase in myocyte number, which continues until shortly after birth, when cardiac myocytes lose their proliferative capacity. Further growth occurs through hypertrophy of the individual cells. Hypertrophy of adult cardiac ventricular myocytes is a response to a variety of conditions which lead to chronic hemodynamic overload. Thus, in response to hormonal, physiological, hemodynamic, and pathological stimuli, adult ventricular muscle cells can adapt to increased workloads through the activation of a hypertrophic process. This response is characterized by an increase in myocyte cell size and contractile protein content of individual cardiac muscle cells, without concomitant cell division and activation of embryonic genes, including the gene for atrial natriuretic peptide (ANP). Cardiac hypertrophy due to chronic hemodynamic overload is the common end result of most cardiac disorders and a consistent feature of cardiac failure. Cardiac hypertrophy is a significant risk factor for both mortality and morbidity in the clinical course of heart failure.

Accordingly, the term "hypertrophy", as used herein, is defined as "is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth.

Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility, etc.), appears to play a critical role in determining the nature of the response. The early stage of cardiac hypertrophy is usually characterized morphologically by increases in the size of mycrofibrils and mitochondria, as well as enlargement of mitochondria and nuclei. At this stage, while muscle cells are larger than normal, cellular organization is largely preserved. At a more advanced stage of cardiac hypertrophy, there are preferential increases in the size or number of specific organelles, such a mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. In certain aspects, the cardiac hypertrophy may result from any cause, including idiopathic, cardiotrophic, or myotrophic causes, or ischemia or ischemic insults, such as myocardial infarction. In certain aspects of a method of treating cardiac hypertrophy in a subject in need of treatment thereof comprising administering to the subject an effective amount of a small molecule inhibitor of HuR-mRNA interaction (including but not limited to KH-3, CMLD-1, CMLD-2, or a combination thereof), the cardiac hypertrophy is associated with a pathological condition selected from hypertension, aortic stenosis, myocardial infarction, cardiomyopathy (including hypertrophic cardiomyopathy), valvular regurgitation, cardiac shunt, and heart failure (including congestive heart failure).

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" is a progressive pathologic state where the heart is increasingly unable to supply adequate cardiac output (the volume of blood pumped by the heart over time) to deliver the oxygenated blood to peripheral tissues. As congestive heart failure progresses, structural and hemodynamic damages occur. While these damages have a variety of manifestations, one characteristic symptom is ventricular hypertrophy. Congestive heart failure is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As used herein, the term "treating," "treatment," and the like relate to any treatment of cardiac hypertrophy, including but not limited to prophylactic treatment and therapeutic treatment. "Treating" includes any effect, e.g., lessening, reducing, modulating, or eliminating, that results in the improvement of the cardiac hypertrophy. "Treating" or "treatment" of cardiac hypertrophy includes: inhibiting the inhibiting the cardiac hypertrophy, i.e., arresting the development of the cardiac hypertrophy or its clinical symptoms; or relieving the cardiac hypertrophy, i.e., causing temporary or permanent regression of the cancer or its clinical symptoms. Those in need of treatment include those already with cardiac hypertrophy and those in whom cardiac hypertrophy is to be prevented. As described previously, in aspects the cardiac hypertrophy may result from any cause, including idiopathic, cardiotrophic, or myotrophic causes, or ischemia or ischemic insults, such as myocardial infarction, and the cardiac hypertrophy may be associated with a pathological condition such as hypertension, aortic stenosis, myocardial infarction, cardiomyopathy (including hypertrophic cardiomyopathy), valvular regurgitation, cardiac shunt, and heart failure (including congestive heart failure).

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). A "subject in need thereof" refers to a subject who may have, is diagnosed with, is suspected of having, or requires prevention of cardiac hypertrophy. In aspects, the cardiac hypertrophy may result from any cause, including idiopathic, cardiotrophic, or myotrophic causes, or ischemia or ischemic insults, such as myocardial infarction, and the cardiac hypertrophy may be associated with a pathological condition such as hypertension, aortic stenosis, myocardial infarction, cardiomyopathy (including hypertrophic cardiomyopathy), valvular regurgitation, cardiac shunt, and heart failure (including congestive heart failure). In certain embodiments of a method of treating cardiac hypertrophy in a subject in need of treatment thereof comprising administering to the subject an effective amount of a small molecule inhibitor of HuR-mRNA interaction (including but not limited to KH-3, CMLD-1, CMLD-2, or a combination thereof), the subject or subject in need thereof that is administered an effective amount is a mammal.

An "effective amount" or a "therapeutically effective amount" is defined herein in relation to the treatment of cardiac hypertrophy is an amount that when administered alone or in combination with another therapeutic agent to a cell, tissue, or subject is effective to decrease, reduce, inhibit, or otherwise abrogate the growth of the cardiac hypertrophy. An "effective amount" further refers to that amount of the compound sufficient to result in amelioration of symptoms, e.g., treatment, healing, prevention, or amelioration for the cardiac hypertrophy, or in increase in the rate of treatment, healing, prevention, or amelioration of cardiac hypertrophy. When applied to an individual compound (active ingredient) administered alone, an "effective amount" refers tot that ingredient alone. When applied to a combination, the "effective amount" refers to combined amounts of the active ingredients that result in the therapeutic effect, whether administered in combination, serially, or simultaneously. The "effective amount" will vary depending the cause of the cardiac hypertrophy (which can include, but is not limited to, idiopathic, cardiotrophic, or myotrophic causes, or ischemia or ischemic insults, such as myocardial infarction) and the severity of the cardiac hypertrophy, as well as the age, weight, etc., of the mammal to be treated. Additionally, the "effective amount" can vary depending upon the dosage form employed and the route of administration utilized. A physician or veterinarian having ordinary skill in the art can readily determine and prescribe the effective amount (e.g., ED50) of the active ingredients required. For example, the physician or veterinarian can start doses of the administered compounds at levels lower than that required in order to achieve the desired therapeutic effect and gradually increase the dosage until the desired effect is achieved.

It will be understood that a small molecule inhibitor of HuR-mRNA interaction (including but not limited to KH-3, CMLD-1, CMLD-2, or a combination thereof) can include pharmaceutically acceptable salts, solvates, stereoisomers, and optical isomers thereof. It will further be understood that the small molecule inhibitor of HuR-mRNA interaction (including but not limited to the compounds KH-3, CMLD-1, CMLD-2, or a combination thereof) can include prodrugs of such compounds.

"Pharmaceutically acceptable salt" of a compound means a salt that is pharmaceutically acceptable and that possesses the desired pharmacological activity of the parent compound. As used herein, "pharmaceutically acceptable salt" refers to derivatives of the small molecule inhibitor of HuR-mRNA interaction (including but not limited to the compounds KH-3, CMLD-1, CMLD-2, or a combination thereof), wherein such compounds are modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

It should be understood that all references to a small molecule inhibitor of HuR-mRNA interaction (including but not limited to KH-3, CMLD-1, CMLD-2, or a combination thereof), or pharmaceutically acceptable salts thereof, include solvent addition forms (solvates) or crystal forms (polymorphs) as defined herein.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, a small molecule inhibitor of HuR-mRNA interaction (including but not limited to the compounds KH-3, CMLD-1, CMLD-2, or a combination thereof) can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The small molecule inhibitors of HuR-mRNA interaction (including but not limited to KH-3, CMLD-1, CMLD-2, or a combination thereof) can be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) The small molecule inhibitor of HuR-mRNA interaction (including but not limited to KH-3, CMLD-1, CMLD-2, or a combination thereof) can be delivered in prodrug form. Thus, the instant methods are intended to cover the use of prodrugs of small molecule inhibitors of HuR-mRNA interaction (including but not limited to KH-3, CMLD-1, CMLD-2, or a combination thereof). "Prodrugs" are intended to include any covalently bonded carriers that release an active parent drug of the present invention in vivo when such prodrug is administered to a subject.

In some embodiments of a method of treating cardiac hypertrophy in a subject in need of treatment thereof comprising administering to the subject an effective amount of a small molecule inhibitor of HuR-mRNA interaction (including but not limited to compounds KH-3, CMLD-1, CMLD-2, or a combination thereof), the effective amount of the small molecule inhibitor of HuR-mRNA interaction is administered with at least one pharmaceutically acceptable excipient and/or at least one pharmaceutically acceptable carrier that are suitable for administration by various routes. It should be understood that in embodiments of a method of treating cardiac hypertrophy in a subject in need of treatment thereof comprising administering to the subject an effective amount of a small molecule inhibitor of HuR-mRNA interaction (including but not limited to compounds KH-3, CMLD-1, CMLD-2, or a combination thereof) the small molecule inhibitor of HuR-mRNA interaction can be formulated into compositions that are compatible with the particular route of administration chosen. Thus, these compositions can include carriers, excipients, additives, and diluents suitable for administration by various routes.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Thus, the term "pharmaceutical excipient" is used herein to describe any ingredient other than the delivered active ingredients (e.g., a small molecule inhibitor of HuR-mRNA interaction (including but not limited to compounds KH-3, CMLD-1, CMLD-2, or a combination thereof)). Examples of pharmaceutical excipients include one or more substances which may act as diluents, flavoring agents, solubilisers, lubricants, suspending agents, binders, preservatives, wetting agents, tablet disintegrating agents, or an encapsulating material. The choice of excipient will to a large extent depend on factors such as the particular mode of administration, the effect of the excipient on solubility and stability, and the nature of the dosage form. A "pharmaceutical excipient" includes both one and more than one such excipient.

In some embodiments of a method of treating cardiac hypertrophy in a subject in need of treatment thereof comprising administering to the subject an effective amount of a small molecule inhibitor of HuR-mRNA interaction (including but not limited to compounds KH-3, CMLD-1, CMLD-2, or a combination thereof), the effective amount of the small molecule inhibitor of HuR-mRNA interaction and at least one pharmaceutical excipient described herein can be formulated with a pharmaceutically acceptable carrier for administration to a human or an animal. "Pharmaceutically acceptable carriers" are physiologically acceptable to the administered patient and retain the therapeutic properties of the active ingredients (e.g., a small molecule inhibitor of HuR-mRNA interaction (including but not limited to compounds KH-3, CMLD-1, CMLD-2, or a combination thereof) and any additional active ingredient) with which it is administered. Pharmaceutically-acceptable carriers and their formulations are known to one of ordinary skill in the art. One exemplary pharmaceutical carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antibodies or peptides from the administration site of one organ, or portion of the body, to another organ, or portion of the body. Each carrier must be "acceptable" in the sense of being compatible with the other ingredients of the formulation and not injurious to the patient. Nor should a pharmaceutically acceptable carrier alter the specific activity of the antagonists. Exemplary carriers and excipients are been provided throughout this disclosure.

In embodiments, a small molecule inhibitor of HuR-mRNA interaction (including but not limited to compounds KH-3, CMLD-1, CMLD-2, or a combination thereof) and optionally at least one pharmaceutical excipient and/or pharmaceutically acceptable carrier can be administered with (e.g., in compositions that include) solvents (aqueous or non-aqueous), solutions, emulsions, dispersion media, coatings, isotonic and absorption promoting or delaying agents, compatible with pharmaceutical administration are contemplated. In further embodiments, the a small molecule inhibitor of HuR-mRNA interaction (including but not limited to compounds KH-3, CMLD-1, CMLD-2, or a combination thereof) and optionally at least one pharmaceutical excipient and/or pharmaceutically acceptable carrier can be administered with (e.g., in compositions that include) a pharmaceutically acceptable additive in order to improve the stability of the antagonist in composition and/or to control the release rate of the composition. Pharmaceutically acceptable additives of do not alter the specific activity of the active ingredients. Pharmaceutically acceptable additives include a sugar such as mannitol, sorbitol, glucose, xylitol, trehalose, sorbose, sucrose, galactose, dextran, dextrose, fructose, lactose and mixtures thereof. Pharmaceutically acceptable additives can be combined with pharmaceutically acceptable carriers and/or excipients such as dextrose. Pharmaceutically acceptable additives further include surfactants, such as but not limited to, polysorbate 20 or polysorbate 80.

Formulations/compositions of the small molecule inhibitor of HuR-mRNA interaction (including but not limited to compounds KH-3, CMLD-1, CMLD-2, or a combination thereof) used in the methods of treating cardiac hypertrophy in a subject in need of treatment thereof include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. Formulations for in vivo administration are sterile. Sterilization can be readily accomplished via filtration through sterile filtration membranes. The dosage of a small molecule inhibitor of HuR-mRNA interaction (including but not limited to compounds KH-3, CMLD-1, CMLD-2, or a combination thereof) will vary according to the extent and severity of the need for treatment, the activity of the administered composition, the age, sex, weight, condition, general health, and prior medical history of the subject, other active ingredients and materials used in combination with the small molecule inhibitor of HuR-mRNA interaction, and other considerations well known to the skilled artisan. As such, a small molecule inhibitor of HuR-mRNA interaction (including but not limited to compounds KH-3, CMLD-1, CMLD-2, or a combination thereof) and at least one pharmaceutically acceptable excipient and/or pharmaceutically acceptable carrier can be administered orally as a solid or as a liquid, or can be administered intramuscularly or intravenously as a solution, suspension, or emulsion. Alternatively, the pharmaceutical compositions can be administered by inhalation, intravenously, or intramuscularly as a liposomal suspension. In some embodiments, the pharmaceutical composition is formulated for oral administration. In other embodiments, the pharmaceutical composition is formulated for intravenous administration.

As such, modes of administration of a small molecule inhibitor of HuR-mRNA interaction (including but not limited to compounds KH-3, CMLD-1, CMLD-2, or a combination thereof) include, but are not limited to, injection, infusion, inhalation (e.g., intranasal or intratracheal), ingestion, rectal, and topical (including buccal and sublingual) administration. Local administration can be used to, for example, permit a high localized concentration of the compounds to the site of the cardiac hypertrophy. Administration to deliver compounds of the combination therapy systemically or to a desired surface or target can include, but is not limited to, injection, infusion, instillation, and inhalation administration. Injection includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Therefore, in some embodiments of a method of treating cardiac hypertrophy in a subject in need of treatment thereof, the small molecule inhibitor of HuR-mRNA interaction (including but not limited to compounds KH-3, CMLD-1, CMLD-2, or a combination thereof) can be administered systemically. For example, in some embodiments of a method of treating cardiac hypertrophy in a subject in need of treatment thereof, the small molecule inhibitor of HuR-mRNA interaction are administered orally. In accordance with the presently disclosed methods, the small molecule inhibitor of HuR-mRNA interaction can be administered orally as a solid or as a liquid. In other embodiments of treating cardiac hypertrophy in a subject in need of treatment, the small molecule inhibitor of HuR-mRNA interaction thereof is administered intravenously. In accordance with the presently disclosed methods, the small molecule inhibitor of HuR-mRNA interaction can be administered intravenously as a solution, suspension, or emulsion. Alternatively, in some embodiments of treating cardiac hypertrophy in a subject in need of treatment, the small molecule inhibitor of HuR-mRNA interaction also can be administered by inhalation, intravenously, or intramuscularly as a liposomal suspension.

Formulations/compositions for enteral (oral) administration can be contained in a tablet (coated or uncoated), capsule (hard or soft), microsphere, emulsion, powder, granule, crystal, suspension, syrup or elixir. Conventional non-toxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. A liquid formulation can also be used for enteral administration. The carrier can be selected from various oils including, but not limited to, petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include stabilizers. For example, the solution can contain sodium acetate, sodium lactate, sodium chloride, potassium chloride, calcium chloride, sorbitan monolaurate or triethanolamine oleate. The parenteral preparation can be enclosed in ampules, disposable syringes or multiple dose vials made of glass or plastic.

Pharmaceutical compositions for intradermal or subcutaneous administration can include, but are not limited to including, a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions or dispersions and sterile powders for the extemporaneous preparation of sterile injectable solutions or dispersion. For intravenous administration, suitable carriers include, but are not limited to, physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Isotonic agents, for example, sugars, polyalcohols such as mannitol, sorbitol, and sodium chloride may be included in the composition.

The resulting solutions can be packaged for use as is, or lyophilized; the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known to those of skill in the art.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories. For transdermal administration, the active compound(s) can be formulated into ointments, salves, gels, or creams as generally known in the art.

Transdermal delivery systems can also be achieved using patches.

For inhalation delivery, the formulation/compositions can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. Liposomal suspensions (including liposomes targeted to cells or tissues using antibodies or viral coat proteins) can also be used as pharmaceutically acceptable carriers. These can be prepared according to methods known in the art. Biodegradable microspheres or capsules or other biodegradable polymer configurations capable of sustained delivery of small molecules are also known in the art. Liposomal and lipid-containing formulations can be delivered by any means, including, for example, intravenous, transdermal, transmucosal, or oral administration.

Sustained-release preparations can be prepared as are known in the art. Suitable examples of sustained-release preparations include, but are not limited to, semipermeable matrices of solid hydrophobic polymers, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels can release proteins for shorter time periods.

In some embodiments of a method of treating cardiac hypertrophy in a subject in need of treatment thereof comprising administering to the subject an effective amount of a small molecule inhibitor of HuR-mRNA interaction (including but not limited to compounds KH-3, CMLD-1, CMLD-2, or a combination thereof), the method further comprises administering to the subject one or more additional therapeutic compounds. It will be appreciated that therapeutic benefits for the treatment of cardiac hypertrophy can be realized by combining treatment with a small molecule inhibitor of HuR-mRNA interaction (including but not limited to compounds KH-3, CMLD-1, CMLD-2, or a combination thereof) with one or more additional therapeutic compounds. The term "additional therapeutic compounds" includes traditional treatments for cardiac hypertrophy, including but not limited to, β-adrenergic receptor blocking drugs and calcium channel blockers. In embodiments, β-adrenergic receptor blocking drugs include, but are not limited to, propranolol, timolol, tertalolol, carteolol, nadolol, betaxolol, penbutolol, acetobutolol, atenolol, metoprolol, carvedilol, etc). In embodiments, calcium channel blockers include, but are not limited to, verapamil, nifedipine, diltiazem, etc. The choice of such combinations will depend on various factors including, but not limited to, cause of the cardiac hypertrophy (which can include, but is not limited to, idiopathic, cardiotrophic, or myotrophic causes, or ischemia or ischemic insults, such as myocardial infarction) and the severity of the cardiac hypertrophy, as well as the age, and general health of the subject to be treated, and the ability of the subject to tolerate the agents that comprise the combination. Additionally, in some embodiments of a method of treating cardiac hypertrophy in a subject in need of treatment thereof comprising administering to the subject an effective amount of a small molecule inhibitor of HuR-mRNA interaction (including but not limited to compounds KH-3, CMLD-1, CMLD-2, or a combination thereof), the method can be combined with other agents and therapeutic regimens that are effective at reducing cardiac hypertrophy, including but not limited to septal myectomy, ethanol ablation, and the use of an Implantable Cardioverter Defibrillator.

The additional therapeutic compounds can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

In other embodiments of the presently-disclosed subject matter, a method of a method of inhibiting Human antigen R (HuR) in a cardiomyocyte cell is provided, the method comprising contacting the cell with an effective amount of effective amount of effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof. In some embodiments, the cardiac myocyte cell is a mammalian cell. In further aspects, the cardiac myocyte cell is a human cell. In some aspects, the KH-3, CMLD-1, CMLD-2, or a combination thereof inhibits the activity of HuR by at least about 10%, 25%, 30%, 35%, 40%, 45%, 50%, 55%, 60%, 65%, 70%, 75%, 80%, 85%, 90%, 95% 99%, or any value or range in between.

In other embodiments of the presently-disclosed subject matter, a method of inhibiting nuclear factor activated T cells (NFAT) in a cell is provided, the method comprising contacting the cell with an effective amount of effective amount of effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof. In some embodiments, the cell is a mammalian cell. In some embodiments, the cell is a cardiac myocyte. In some embodiments, the cardiac myocyte cell is a mammalian cell. In further aspects, the cardiac myocyte cell is a human cell. In some aspects, the KH-3, CMLD-1, CMLD-2, or a combination thereof inhibits the activity of NFAT by at least about 10%, 25%, 30%, 35%, 40%, 45%, 50%, 55%, 60%, 65%, 70%, 75%, 80%, 85%, 90%, 95% 99%, or any value or range in between.

In other embodiments of the presently-disclosed subject matter, a method of inhibiting NFAT in a subject in need thereof is provided, the method comprising administering to the subject an effective amount of effective amount of a small molecule inhibitor of HuR-mRNA interaction. In embodiments, the small molecule inhibitor of HuR-mRNA interaction is KH-3. In some embodiments, the small molecule inhibitor of HuR-mRNA interaction is selected from the group consisting of KH-3, CMLD-1, CMLD-2, or a combination thereof. In some aspects, the KH-3, CMLD-1, CMLD-2, or a combination thereof inhibits the activity of NFAT by at least about 10%, 25%, 30%, 35%, 40%, 45%, 50%, 55%, 60%, 65%, 70%, 75%, 80%, 85%, 90%, 95% 99%, or any value or range in between. The KH-3, CMLD-1, CMLD-2, or a combination thereof can be administered to the subject as previously described.

Further aspects of the presently-disclosed subject matter are directed to novel assays and methods of screening for small molecule inhibitors of RNA binding proteins and their interaction with their target RNA. In more specific aspects, the novel assays and screening methods are directed to screening for small molecule inhibitors of HuR-mRNA interaction. As previously discussed, RNA binding proteins were originally thought to be "un-druggable" targets. However, the instantly disclosed data demonstrates the administration of effective amount of a small molecule inhibitor of HuR-mRNA interaction (including but not limited to KH-3, CMLD-1, CMLD-2, or a combination thereof), inhibits Gq-mediated hypertrophic growth of NRVMs as measured by cell size and expression of ANF. Additionally, HuR overexpression is sufficient to induce hypertrophic cell growth. To decipher the downstream mechanisms by which HuR translocation promotes cardiomyocyte hypertrophy, we assessed the role of HuR in the transcriptional activity of NFAT (nuclear factor of activated T cells), the activation of which is a hallmark of cardiac hypertrophy. Using an NFAT-luciferase reporter assay, we show an acute inhibition of NFAT transcriptional activity following pharmacological inhibition of HuR using a small molecule inhibitor of HuR-mRNA interaction (including but not limited to KH-3, CMLD-1, CMLD-2, or a combination thereof). In conclusion, the results identify HuR as a novel mediator of cardiac hypertrophy downstream of the Gq-p38 MAPK pathway, and suggest modulation of NFAT activity as a potential mechanism. Thus, the data demonstrates that the RNA-binding protein HuR is a novel mediator of pathological cardiac hypertrophy and eventual heart failure is a novel therapeutic target for cardiac hypertrophy and eventual heart failure. Based on the presently-disclosed data, small molecule inhibitors of HuR-mRNA interaction (including but not limited to KH-3, CMLD-1, CMLD-2, or a combination thereof), may yield favorable therapeutic indices in patients suffering with cardiac hypertrophy and related poathological cardiac conditions such as hypertension, aortic stenosis, myocardial infarction, cardiomyopathy (including hypertrophic cardiomyopathy), valvular regurgitation, cardiac shunt, and heart failure (including congestive heart failure). Thus, while originally thought to be "un-druggable" targets, our data demonstrates the importance of discovery new small molecule inhibitors of RNA binding proteins and their interaction with target RNA, such as HuR-mRNA interaction. However, currently no approved therapeutics exists that are able to specifically inhibit RNA binding proteins. Therefore, novel assays and methods of screening for compounds for inhibition of RNA binding proteins and their interaction with their target RNA, including HuR-mRNA interactions, are of great interest.

The presently-disclosed data is directed to a novel multiplexed, plasmonic nanoparticle-based assay (and methods of screening drug candidates utilizing such assays) suitable for high-throughput screening of drug candidates to inhibit RNA binding proteins through a simple colorimetric (localized surface plasmon resonance (LSPR)) detection method. Gold nanoparticle arrays, 100 nm in diameter and 60 nm in height, were fabricated using Hole Mask Colloidal Lithography as described previously (Fredricksson H, et al., *Hole-Mask Colloidal Lithography*. Adv Mater. 2007; 19:4297-4302, the entire disclosure of which is incorporated herein by this citation). The nanoparticle arrays are first functionalized with RNA or DNA (e.g., single stranded DNA) for the purpose of secondary RNA tethering. Thus, DNA or RNA is covalently bound directly to the surface of the gold, using either thiolated DNA (or RNA) or EDC coupling of DNA (or RNA) to hybridize the DNA (or RNA) to the nanoparticle surface. In the case of the nanoparticle assay being first functionalized with DNA (e.g., single standed DNA), a RNA strand (e.g., mRNA) containing a HuR target binding site (e.g., a hairpin loop containing a HuR target binding site) was hybridized to the nanoparticle-bound DNA. This occurs because the RNA contains a DNA hybridizing region, which binds via base pair matching, with the DNA on the nanoparticle. HuR protein binding to its target site within the RNA (e.g., within the RNA hairpin loop) can be detected by observing a LSPR shift induced by the increased mass bound to the gold nanoparticle surface. For each step of the assembly, a significant LSPR absorbance shift was observed with the addition of DNA, mRNA, and HuR protein to the nanoparticle surface. Importantly, we are able to quantitatively demonstrate a reversal of HuR-mRNA binding in the presence a HuR-mRNA inhibitor, CMLD-1. The data demonstrates the initial application of this approach to specifically screen for inhibitors of the mRNA binding protein HuR. However, it should be understood that the instantly-disclosed assay provides a flexible platform for high-throughput screening of drug candidates to inhibit both RNA and DNA binding proteins that is applicable to many RNA or DNA binding proteins by simply changing the RNA or DNA target sequence and the RNA or DNA binding protein of interest.

Sagle et al., recently developed a fabrication technique which allows uniform nanoparticle arrays to be incorporated into microfluidic devices based on localized surface plasmon resonance (LSPR biosensing) (WO 2017/031303, the entire disclosure of which is incorporated herein by this citation). However, to date, LSPR-based technology has not been applied to drug screening applications in a multiplexed manner. Techniques commonly used for drug screening include Enzyme-Linked Immunosorbant Assays (ELISA) and SPR-based assays. The former is expensive, time-consuming and involves labeling. The latter lacks the ease and portability of colorimetric detection and has limited multiplexing capabilities. Label-free, highly multiplexed assays are critically needed for such applications since they enable small amounts of compounds to be run directly and simultaneously, reducing the risk of false readings, generating rapid read-out with less cost. The instantly disclosed nanoparticle arrays are surface-bound and colored, the substrates require very small volumes, can be facedly washed and regenerated, and provide rapid read-out. The instantly-disclosed assay will prove extremely useful and suitable for the rapid, facile identification of lead compounds for HuR inhibition, and as previously mentioned, will be easily adaptable to screen for binding inhibition of nearly any RNA binding protein. Further, it should be understood that the instantly-disclosed assay will prove extremely useful and suitable for the rapid, facile identification of screening of lead compounds for binding inhibition of nearly any DNA binding protein.

Accordingly, the presently-disclosed subject matter includes LSPR biosensor-based assays suitable for assaying samples for an inhibitor of a RNA binding protein or a DNA binding protein. In some embodiments the assay comprises an LSPR biosensing microfluidic channel device as described herein. The nanoparticle arrays surface is functionalized with target RNA (or DNA with the purpose of secondary target RNA tethering to the DNA) when assaying for inhibitors of RNA binding protein, or the nanoparticle arrays surface is functionalized with target DNA when assaying for inhibitors of DNA binding protein. When assaying for inhibitors of RNA binding protein, a RNA binding protein of interest that is specific to the target RNA is added to the assay. When assaying for inhibitors of DNA binding protein, a DNA binding protein of interest that is specific to the target DNA is added to the assay. A candidate of interest (e.g., a small molecule of interest) is added to the channels, and a change in LSPR signal is detected, wherein detecting is effectuated by an ultraviolet to visual spectrometer. Importantly, attachment of target RNA (or the secondary RNA binding to attached DNA) or target DNA can be confirmed by an observed LSPR shift. Addition of an RNA binding protein or DNA binding protein then results in a further LSPR shift upon binding to surface-coupled target RNA or surface-coupled target DNA, respectively. This shift upon the RNA binding protein (e.g. HuR) to its target RNA (or upon the DNA binding protein to its target DNA) is absent in the presence of a candidate of interest that acts as an inhibitor. In some aspects, the shift upon RNA binding protein (e.g. HuR) to its target RNA (or upon the DNA binding protein to its target DNA) is reduced in the presence of a candidate of interest that acts as an inhibitor. It should be understood that the instantly-disclosed assay will prove extremely useful and suitable for the rapid, facile identification of screening of lead compounds for binding inhibition of nearly any RNA binding protein or DNA binding protein. The LSPR biosensing microfluidic devices and/or LSPR biosensing well plates fabricated according to embodiments of the inventive methods area also contemplated and further described.

Broad aspects for fabricating a localized surface plasmon resonance (LSPR) biosensing device comprising a plurality of plasmonic nanoparticle arrays to be surface functionalized with target RNA (or DNA with the purpose of secondary RNA tethering to the DNA) when assaying for inhibitors of RNA binding protein, or the functionalized with target DNA when assaying for inhibitors of DNA binding protein, comprise: patterning device channels and/or wells onto a substrate with photolithography; and patterning uniform nanoparticle arrays onto the substrate with hole-mask colloidal lithography.

In aspects, a localized surface plasmon resonance (LSPR) biosensing device comprising a plurality of plasmonic nanoparticle arrays to be surface functionalized with RNA (or DNA with the purpose of secondary RNA tethering to the DNA) when assaying for inhibitors of RNA binding protein, or the functionalized with target DNA when assaying for inhibitors of DNA binding protein can be fabricated through a method comprising (a) transferring a desired pattern to a photoresist on a substrate using photolithography; (b) spin coating a poly(methylmethacrylate) (PMMA) over the patterned photoresist and spin coating poly(diallyldimethylammonium chloride) (PDDA) over the PMMA to create a polymer layer; (c) drop coating a plurality of polystyrene particles of a desired shape and size on the polymer layer; (d) depositing a nanomeric layer of gold; (e) removing the polystyrene particles to create a hole-mask; (f) etching the hole mask to generate a plurality of holes; (g) depositing a metal into the holes; and (h) removing the polymer layer and the photoresist to yield a plurality of nanoparticle arrays in a desired pattern. The nanoparticle surface of the (LSPR) biosensing device comprising a plurality of plasmonic nanoparticle arrays is subsequently (i) functionalized with RNA (or DNA with the purpose of secondary RNA tethering to the DNA) when assaying for inhibitors of RNA binding protein, or the functionalized with target DNA when assaying for inhibitors of DNA binding protein. Further, (j) a candidate of interest (e.g., a small molecule of interest) is added to the channels, and (k) a change in LSPR signal is detected, wherein detecting is effectuated by an ultraviolet to visual spectrometer. As described previously, attachment of target RNA (or DNA with the purpose of secondary RNA tethering to the DNA) when assaying for inhibitors of RNA binding protein, or the functionalized with target DNA when assaying for inhibitors of DNA binding protein can be confirmed by an observed LSPR shift. Addition of an RNA binding protein (or DNA binding protein when using target DNA) then results in a further LSPR shift upon binding to surface-coupled target RNA (or surface-coupled DNA). This shift upon binding of the RNA binding protein (e.g. HuR) to target RNA (or upon binding of the DNA binding protein to target DNA) is absent in the presence of a candidate interest that acts as an inhibitor, herein an "agent" as described below. In some aspects, the shift upon the RNA binding protein (e.g. HuR) to the target RNA (or the DNA binding protein to the target DNA) is reduced in the presence of a candidate of interest that acts as an inhibitor, or an agent. In further aspects, a second nanoparticle (e.g., a gold nanoparticle) with DNA (e.g., single stranded DNA) hybridized to its surface (through the use of EDC coupling or thiolated DNA, as described below), can be bound to the end of the target RNA in order to amplify the observed LSPR shifts. The RNA itself will be used to tether a second gold nanoparticle to the surface-bound nanoparticle through interactions at both ends with the DNA probe strands. The LSPR biosensing microfluidic devices and/or LSPR biosensing well plates fabricated according to embodiments of the inventive methods area also contemplated and further described.

Conventional localized plasmon resonance biosensors include a plurality of metal particles arranged on a substrate in a defined pattern. When light is radiated to these metal particles, it causes a resonant vibration of free electrons in the metal particles with a vibrating frequency of electric field of the light, and plasmon excitation occurs around the surfaces of the metal particles. The condition of localized plasmon resonance in this state is determined by the size of the metal particles and a dielectric constant around the particles. In a resonant frequency of the localized plasmon resonance, there emerges a peak of light absorption. In the instantly disclosed assays and methods, the metal particles may be functionalized with a target RNA (or DNA with the purpose of secondary RNA tethering to the DNA) when assaying for inhibitors of RNA binding protein, or functionalized with target DNA when assaying for inhibitors of DNA binding protein. Accordingly, attachment of the target RNA (or DNA with the purpose of secondary RNA tethering to the DNA) when assaying for inhibitors of RNA binding protein, or attachment of the target DNA when assaying for inhibitors of DNA binding protein can be confirmed by an observed LSPR shift. Upon coupling, a dielectric constant of the surfaces of the metal particles changes, hence changing the condition of the localized plasmon resonance. Accordingly, an interaction of the target RNA or target DNA can be sensed by detecting a change of an optical response of the metal particles. The optical response includes absorption, scattering, fluorescence, Raman scattering, and harmonic luminescence. Addition of an RNA binding protein of interest that is specific to the target RNA (or DNA binding protein of interest that is specific to the target DNA) then results in a further LSPR shift upon binding to surface-coupled target RNA (or surface coupled target DNA). This shift upon the binding of the RNA binding protein (e.g. HuR) to the target RNA (or upon the binding of the DNA binding protein to the target DNA) is absent in the presence of a candidate of interest that acts as an inhibitor to RNA binding protein-target RNA (e.g., mRNA) interaction (or DNA binding protein-target DNA interaction). In some aspects, the shift upon the RNA binding protein (e.g. HuR) to the target RNA (or the DNA binding protein to the target DNA) is reduced in the presence of a candidate of interest that acts as an inhibitor.

In embodiments, the target RNA (or DNA with the purpose of secondary RNA tethering to the DNA) when assaying for inhibitors of RNA binding protein, or the target DNA when assaying for inhibitors of DNA binding protein, may be attached to a plasmon-resonance nanoparticle surface by EDC coupling or thiolation. In aspects, the method of attaching the target RNA to the surface is accomplished by diluting the target RNA to a desired concentration in MES buffer and covalently linking the target RNA to the nanoparticle surface (e.g., gold nanoparticle surface) via common EDC coupling (Bioconjugate Techniques, Greg T. Hermanson, ISBN: 978-0-12-382239-0, the entire disclosure of which is incorporated herein by this citation). A similar procedure can be used for attaching target DNA to the surface. In aspects, the method of attaching the DNA (with which a secondary target RNA may be bound to) to the surface is accomplished by using thiolated DNA (e.g. thiolated single stranded DNA) which can directly bind to the nanoparticle surface (e.g., gold nanoparticle surface). Additionally, other means of attaching target RNA or DNA to a plasmon-resonance nanoparticle surface are contemplated, and can include covalent bonding or other molecular forces, e.g., electrostatic or dispersion forces. The RNA or DNA is capable of binding to the plasmon-resonance nanoparticle surface without significantly binding to other molecules. In accordance with embodiments of the invention, the nanoparticle surface is said to be "functionalized" upon attachment of the binding partner.

In embodiments, the RNA binding protein is any RNA binding protein of interest. It is understood that the RNA binding protein of interest is capable of binding the target RNA (e.g., target mRNA) that is either directly bound to the nanoparticle surface or that is bound to the DNA that is directly bound to the nanoparticle surface, as previously described. In certain embodiments, the RNA binding protein is HuR. In embodiments, the DNA binding protein is any DNA binding protein of interest. It is understood that the DNA binding protein of interest is capable of binding the target DNA that is directly bound to the nanoparticle surface, as previously described.

The term "sample" as used herein relates to a material or mixture of materials containing one or more candidate of interest. A candidate of interest includes compound (libraries) from which its influence on the complex formation between an RNA binding protein and its target RNA (or DNA binding protein and its target DNA) may be expected, e.g., including (m)RNA fragments, DNA fragments, oligopeptides, polypeptides, proteins, antibodies, mimetics, small molecules, e.g., low molecular weight compounds. An "agent" is one of the chosen candidates of interest that act as an inhibitor to the RNA binding protein-RNA interaction (or DNA binding protein-DNA interaction). In other embodiments, the sample may be obtained from a biological sample such as cells, tissues, bodily fluids, and stool. Bodily fluids of interest include but are not limited to, amniotic fluid, aqueous humor, vitreous humor, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the assay. For example, prior to analysis, the protein/nucleic acid may be extracted from a tissue sample, methods for which are known. In particular embodiments, the sample may be a clinical sample, e.g., a sample collected from a patient. Samples may also consist of an "experimental" sample, i.e., a sample of interest, and a "control" sample to which the experimental sample may be compared.

The term "assaying" refers to testing a sample to detect the presence and/or amount of an candidate in a sample. As used herein, the terms "determining," "measuring," and "assessing," and "assaying" are used interchangeably and include both quantitative and qualitative determinations. The word "detecting" means detecting whether a candidate is present or not in the sample, as well as quantitatively measuring the amount of such a candidate to provide an absolute or relative value, e.g., a value relative to a control sample.

One embodiment of the invention is directed to a method for fabricating a localized surface plasmon resonance (LSPR) biosensing device comprising a plurality of nanoparticle arrays. The method comprises: transferring a desired pattern to a photoresist on a substrate using photolithography; spin coating at least two coats of polymer to form a polymer layer; drop coating a plurality of polystyrene particles of a desired shape and size on the polymer layer; depositing a nanomeric layer of gold; removing the polystyrene particles to create a hole-mask, for example by tape stripping with an adhesive tape; etching the hole mask to generate a plurality of holes; depositing a metal into the holes; and (h) removing the polymer layer and the photoresist to yield a plurality of nanoparticle arrays in a desired pattern. In specific embodiments, suitable plastics/polymers for comprising the polymer layer include e.g., cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA) and polydimethylsiloxane (PDMS). According to a specific embodiment, the method comprises spin-coating a polyacrylate, followed by spin-coating poly(diallyldimethylammonium chloride) (PDDA) over the polyacrylate. In very specific embodiments the polyacrylate comprises poly(m-ethylmethacrylate) (PMMA). The nanoparticle surface of the (LSPR) biosensing device comprising a plurality of plasmonic nanoparticle arrays is subsequently (i) functionalized with RNA (or DNA with the purpose of secondary RNA tethering to the DNA) when assaying for inhibitors of RNA binding protein, or the functionalized with target DNA when assaying for inhibitors of DNA binding protein. Further, (j) a candidate of interest (e.g., a small molecule of interest) is added to the channels, and (k) a change in LSPR signal is detected, wherein detecting is effectuated by an ultraviolet to visual spectrometer. As described previously, attachment of target RNA (or the secondary RNA binding to attached DNA) or target DNA can be confirmed by an observed LSPR shift. Addition of an RNA binding protein or DNA binding protein then results in a further LSPR shift upon binding to surface-coupled target RNA or surface-coupled target DNA, respectively. This shift upon binding of the RNA binding protein to its target RNA (or binding of the DNA binding protein to its target DNA) is absent in the presence of a candidate of interest that acts as an agent (i.e. inhibitor). In some aspects, shift upon binding of the RNA binding protein to its target RNA (or binding of the DNA binding protein to its target DNA) is reduced in the presence of a candidate of interest that acts as an agent (i.e. inhibitor). The LSPR biosensing microfluidic devices and/or LSPR biosensing well plates fabricated according to embodiments of the inventive methods area also contemplated and further described.

In some specific embodiments the LSPR biosensing device is a microfluidic device and the desired pattern comprises microfluidic channels. A poly(dimethylsiloxane) (PDMS) layer comprising a corresponding microfluidic channel pattern is aligned with the substrate. The PDMS layer is then sealed to the substrate in regions that do not contain the nanoparticular arrays. According to other embodiments, the LSPR biosensing device is a spot plate and the desired pattern comprises a spot plate array. A poly(dimethylsiloxane) (PDMS) layer comprising a corresponding spot plate array pattern is aligned the substrate and sealing to the substrate in regions that do not contain the nanoparticle arrays. This prevents between-well sample contamination.

The substrate may be formed from any suitable material including, for example, glass, plastic, flexible plastic and paper. According to specific embodiments, the substrate is glass. Any suitable glass may be used but a preferred substrate has at least a silicon dioxide surface layer. In other specific embodiments the substrate is a flexible plastic. In very specific embodiments, the flexible plastic comprises nitrocellulose acetate. In even more specific embodiments the flexible plastic substrate comprises a flexible plastic strip. The use of flexible plastic substrates permits greater portability, and also renders the devices more adaptable for interfacing with other devices, for example wrapping around optical fibers and optical cables for increased sensitivity. In other very specific applications the flexible plastic substrate platform provides a highly sensitive, portable point-of-care device for assay/diagnosis/screening of patients in regions of limited resources or accessibility or under urgent time frames.

In certain embodiments the nanomeric gold layer is between 1 nm and 10 nm thick, and in very specific embodiments the nanomeric gold layer is 5 nm thick.

The polystyrene spheres may be of the same diameter or different diameters, or size may be distributed in accordance with the needs of an assay. In very specific embodiments the polystyrene particles comprise polystyrene spheres of the same diameter, with the diameter between 1 nm and 40 nm. It is known and predictable that the resonantly scattered wavelength of a spherical particle will increase, or be "red-shifted", with increasing particle diameter and with increasing dielectric constant of the surrounding material. For spherical particles, dipole resonance produces a scattered frequency spectrum having a single peak at a wavelength which is dependent on the material the particle is made from the size of the particle, the shape of the particle, the morphology of the particle, and the local environment. Larger particles have a longer dipole scattering peak wavelength, and smaller particles have a shorter dipole scattering peak wavelength. The spectrum of scattered light may also contain contributions from a particle's quadrupole resonance. For a given shape, a resonant particle scatters predominantly in a particular wavelength band depending on the composition and size of the particle.

The conductive portion responsible for the plasmons can take many different forms, including solid geometric shapes such as spheres, triangular parallelepipeds, ellipsoids, tetrahedrons, and the like, or may comprise spherical, cylindrical, or other shape shells. A dielectric sphere of similar dimensions, having a suitable metal on its surface exhibits plasmon resonances, assuming the shell has a thickness of at least about 3 nm, preferably 5 nm or more of the metal. The metal may be gold, silver, platinum, palladium, lead, iron, titanium, nickel, copper, aluminum, alloy thereof, or combinations thereof, although other materials may be used, as long as the materials' plasma frequency is higher than that of the light signal and the light that is used to generate the light signal. In specific embodiments the metal is silver or gold, and in very specific embodiments the metal is gold. In certain embodiments, where silver is selected, the silver is coated with functionalized silica.

The nanoparticle array may be fabricated for miniaturized applications, for example on a chip. In specific embodiments the array is circular and has a diameter of between about 20 nm and about 400 nm or a non-circular area of between about 320 $nm^2$ and about 12600 $nm^2$.

According to some embodiments, LSPR biosensor-based assays suitable for simultaneously assaying two or more samples for a candidate of interest are provided. A candidate of interest is as described previously, and may be located in a sample, as described previously. A microfluidic device embodiment of the invention is fabricated. The channels of the microfluidic device comprise liquid test samples and test reagents (such as detection proteins, detection nucleic acids, light labels, solvents, blocking solutions, etc). The microfluidic device can have multiple fluidic channels. Each of the fluidic channels can have zero, one, or more than one nanoarrays. Fluidic channels may be oriented in different directions depending on the need of the assay. Basic functions such as transportation, mixing, or separation of a fluid in a quantity desired by a user, are typically performed by using a valve or a pump system. To operate the valve or pump system of a microfluidic device, thermal, magnetic, electrical, or pneumatic methods may be used. The surfaces of the nanoparticles of the nanoparticle arrays are functionalized with target RNA or target DNA and used as previously described. The microfluidic devices manufactured according to embodiments of the instantly-disclosed methods provide sufficiently salient signal to be detected by a simple ultraviolet to visual spectrometer.

Another embodiment of a microfluidic device provides a platform for measurement of kinetics of multiple analytes. According to specific embodiments the analytes become kinetically bound by flowing solution through small channels simultaneously.

According to other embodiments, LSPR biosensor-based assays suitable for simultaneously assaying a sample for two or more candidates of interest are provided. The spot or well-plate is also sometimes referred to as a microwell plate or microplate and is manufactured according to embodiments of the instant disclosure. A microwell plate typically has 6, 24, 96, 384 or 1536 sample wells. Nanoparticle arrays in the wells are functionalized with target RNA or target DNA and used as described previously. A person of ordinary skill in the art understands that the well plate may be partitioned into different sample areas or different reagent areas or whatever meets assay needs. Control wells and the like may be included. The micro well may be read by a standard plate reader. A change in LSPR signal is detected, as described previously.

EXAMPLES

The following examples are given by way of illustration and are in no way intended to limit the scope of the present invention.

Example 1—Methods of Treating Cardiac Hypertrophy and Related Cardiac Disorders

Material and Methods

Neonatal Rat Ventricular Myocyte Isolation and Cell Culture:

Neonatal rat ventricular myocytes (NRVMs) were isolated using collagenase digestion and adhesion differential from fibroblasts as described (E. Ehler, T. Moore-Morris, S. Lange, Isolation and culture of neonatal mouse cardiomyocytes, J Vis Exp. (2013) e50154-e50154. doi:10.3791/50154, the entire disclosure of which is incorporated herein by this citation). Briefly, Sprague Dawley neonatal rats (1-2 days old) (Taconic) were decapitated and the hearts were isolated. Following removal of the atria, the ventricles were cut into small pieces and digested first in 0.05% trypsin/EDTA (Corning) overnight, then in collagenase II (Gibco) for 30 minutes. Cells were then spun at 100×g followed by a 40 minute pre-plating process on non-treated plates to allow the fibroblasts to adhere. The non-adherent NRVMs were then transferred to cell culture-treated dishes in MEM alpha media (Gibco) with 10% FBS. The study was performed under protocol #13-08-29-01, which has been approved by the University of Cincinnati Institutional Animal Care and Use Committee, and the animals received humane care in compliance with the National Research Council's criteria as outlined in the Guide for the Care and Use of Laboratory Animals prepared by the National Institutes of Health.

HuR siRNA-Mediated Gene Silencing and Overexpression:

To achieve siRNA-mediated knockdown of HuR expression, NRVMs were seeded at ~75% confluency and transfected with HuR or non-targeting control siRNA (80 nM) (Santa Cruz Biotechnology) 24 hours after plating using Lipofectamine 3000 (ThermoFisher Scientific) as per manufacturer's instructions. Cells were grown for 48 hours post-transfection prior to treatment with phenylephrine (PE). To achieve HuR overexpression, the full-length HuR coding region was cloned from mouse cDNA via PCR and inserted into a modified pGL4.1 expression vector driven by a constitutively active CMV promoter. NRVMs were seeded at ~75% confluency and transfected with either HuR overexpression vector or equal amounts of a control vector (coding for overexpression of luciferase). Cells were grown for 24 hours post-transfection prior to treatment with PE. HuR knockdown (>80%) and overexpression (~5-fold, FIG. S1) was confirmed via Western blotting.

RNA Isolation and qRT-PCR:

RNA was isolated using a Macherey-Nagel NucleoSpin RNA kit and cDNA was synthesized using a BioScript All-in-One cDNA Synthesis SuperMix (Biotool). Samples were run on Stratagene Mx3005P (Agilent Technologies) using SYBR Green qPCR Master Mix (Biotool) to assess levels of GAPDH, ANF (atrial natriuretic factor), and RCAN1 (Regulator of Calcineurin 1). Results were analyzed using the ΔΔCt method (K. J. Livak, T. D. Schmittgen, Analysis of relative gene expression data using real-time quantitative PCR and the 2(-Delta Delta C(T)) Method, Methods. 25 (2001) 402-408. doi:10.1006/meth.2001.1262, the entire disclosure of which is incorporated herein by this citation). Primers are as listed:

```
GAPDH,
Forward,
                                            (SEQ ID NO 1)
5'-ACCACAGTCCATGCCATCAC-3', Reverse,
                                            (SEQ ID NO 2)
5'-TCCACCACCCTGTTGCTGTA-3';

ANF,
Forward,
                                            (SEQ ID NO 3)
5'-AGGAGAAGATGCCGGTAG-3', Reverse,
                                            (SEQ ID NO 4)
5'-GCTTTTCAAGAGGGCAGA-3';

RCAN,
Forward,
                                            (SEQ ID NO 5)
5'-GGGCCAAATTTGAATCCCTCTTC-3', Reverse,
                                            (SEQ ID NO 6)
5'-GGAGCCAGGTGTGAACTTCC-3'.
```

Protein Isolation and Western Blotting:

Total protein was isolated from in vitro cell cultures using a solution of 10 mM HEPES, (pH 9), 1.5 mM MgCl2, 10 mM KCl, 0.5 mM DTT, 0.2 mM sodium-orthovanadate, and a protease inhibitor mixture tablet (Complete mini; Roche Applied Science). 25 μg of protein extract per lane was separated on a 10% polyacrylamide gel and transferred to a nitrocellulose membrane. Blocking was performed for 1 hour at room temperature using 5% dry milk in 0.1% Tween 20, tris-buffered saline (T-TBS). Primary antibodies for HuR or GAPDH (Santa Cruz Biotechnology) were incubated overnight at 4° C., and secondary antibodies were incubated for 1-2 h at room temperature in T-TBS.

Immunohistochemistry, Wheat Germ Agglutinin Staining, and Microscopy:

NRVMs were grown on coverslips (pre coated with 0.2% gelatin) in 12-well plates, and treated with PE (10 μM), angiotensin II (AngII, 100 nM), PMA (2 μM), SB203580 (10 μM), or chelerythrine (10 μM) for the indicated amount of time. Following treatment, cells were fixed with 4% paraformaldehyde for 15 minutes, followed by permeabilization with 100% methanol for 15 minutes, dehydration with 70% ethanol for 15 minutes and blocking with 6% bovine serum albumin (BSA) for 1 hour at RT. Cells were incubated in primary antibody for HuR (1:500) for 1 hour at RT followed by secondary antibody for Alexa Fluor 488 (1:2000) (ThermoFisher) for 1 hour at RT. All antibodies were made up in 0.6% BSA in PBS. For wheat germ agglutinin (WGA) staining, a Texas Red-X conjugate was used per manufacturer's instructions (ThermoFisher). All slides were imaged with the BioTek Cytation 3 image reader and quantitative assessment of HuR translocation was measured as the ratio of cytoplasmic to nuclear fluorescent intensity (adjusted for mean background fluorescence and integrated area) using ImageJ.

NFA T-Luciferase Reporter Assays:

NRVMs were transfected with 75 ng per well (in a 96-well plate) of NFAT-luciferase reporter plasmid acquired from AddGene (51941) (B. J. Wilkins et al., Calcineurin/ NFAT coupling participates in pathological, but not physiological, cardiac hypertrophy, Circ. Res. 94 (2004) 110-118. doi:10.1161/01.RES.0000109415.17511.18, the entire disclosure of which is incorporated herein by this citation). 48 hours after transfection, cells were treated with 10 μM PE for 24 hours to induce NFAT reporter activity. To quantify luciferase reporter expression, cells were rinsed with sterile PBS and then lysed with 50 μL Cell Lysis Buffer (Promega) for 5 min at room temperature, followed by addition of 100 μL luciferase assay reagent (Promega); luminescence was read immediately on the BioTek Cytation 3 image reader. HuR inhibitors were previously identified by Wu et. al. (X. Wu et al., *Identification and Validation of Novel Small Molecule Disruptors of HuR-mRNA Interaction*, ACS Chem. Biol. (2015) 150317154550000-9. doi:10.1021/cb500851u. the entire disclosure of which is incorporated herein by this citation), and used here as described.

2.7 Statistical Analysis

All results represent an N of at least 3 per group and are reported as the mean±SEM. Results were analyzed with unpaired Student's t-tests and one-way ANOVA as appropriate. Statistical significance between groups was considered at $P \leq 0.05$.

Results

Figure 1B:
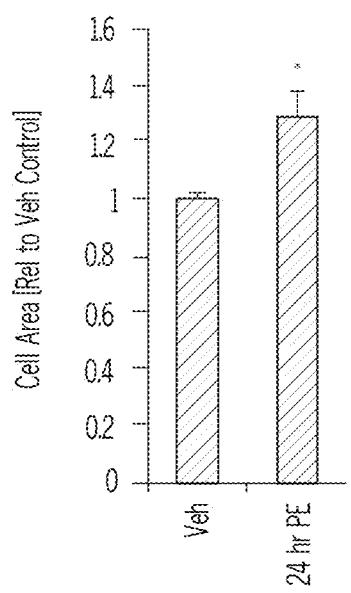
Figure 1C:
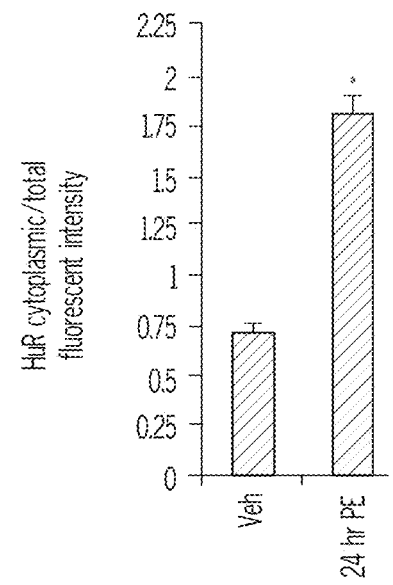

HuR is Activated in Hypertrophic Neonatal Rat Ventricular Myocytes (NRVMs):

HuR activation is regulated by phosphorylation, and activation is commonly marked by translocation from the nucleus to cytoplasm (A. Doller, J. Pfeilschifter, W. Eberhardt, Signalling pathways regulating nucleocytoplasmic shuttling of the mRNA-binding protein HuR, Cell. Signal. 20 (2008) 2165-2173. doi:10.1016/j.cellsig.2008.05.007, the entire disclosure of which is incorporated herein by this citation). Our results show a significant increase in HuR translocation to the cytoplasm in hypertrophic myocytes (FIG. 1). First, we demonstrate an increase in total cell area indicative of hypertrophic cell growth following 24 hours of treatment with 10 μM phenylephrine using wheat germ agglutinin (WGA) staining (1.29±0.08-fold increase in cell area in 24 hr PE-treated cells compared to vehicle treated control cells; $P \leq 0.01$) (FIG. 1A; top panel and FIG. 1B). Next, we show an increase in HuR translocation in hypertrophic NRVMs. HuR nuclearcytoplasmic translocation was quantified following immunostaining by measuring the ratio of cytoplasmic to total cell fluorescent intensity, and is significantly increased in hypertrophic cells (0.71±0.04 in vehicle control vs. 1.82±0.08 in 24 hr PE-treated cells; $P \leq 0.001$) (FIG. 1A; lower panel and FIG. 1C).

Figure 2A:
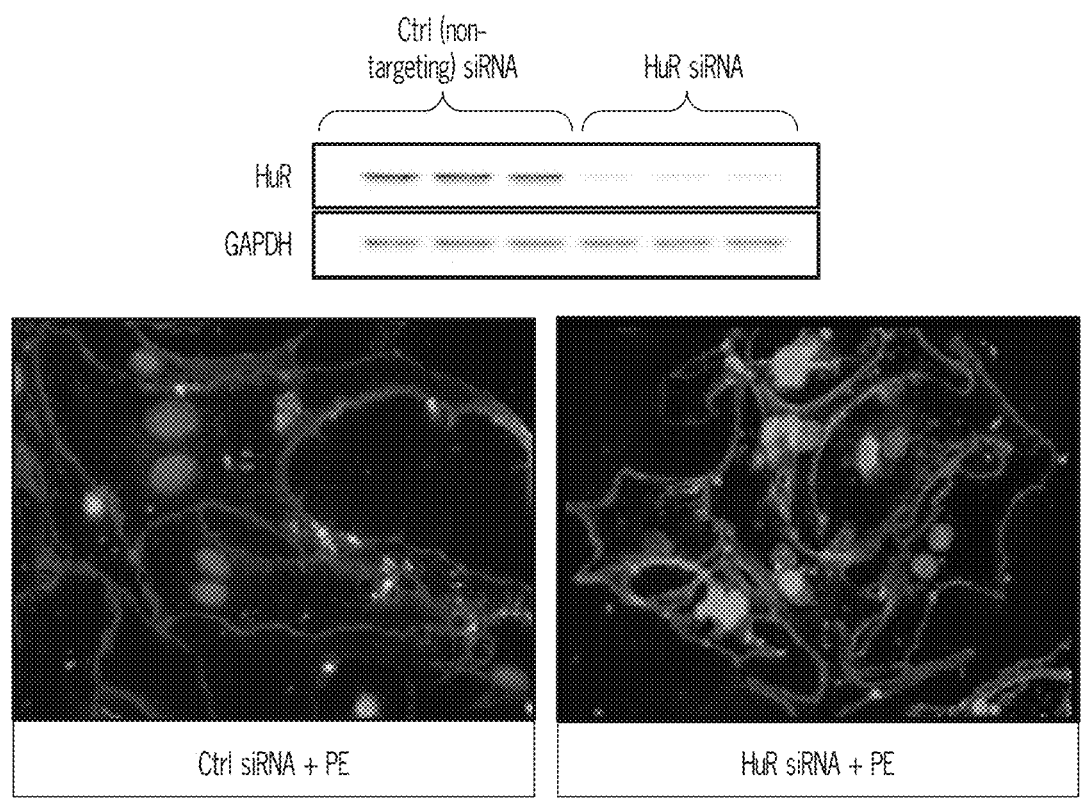
FIG. 2A-C. Knockdown of HuR expression inhibits hypertrophic cell growth. NRVMs were transfected with non-targeting control or HuR siRNA 48 hours prior to treatment with PE for 24 hours to induce hypertrophic cell growth and stained with WGA to determine cell size (FIG. 2A). Cell surface area was quantitatively determined using NIH Image J (FIG. 2B). N≥3 for each group (each N represents the average measurement of 10 cells per well). *P≤0.05. In addition, RNA was isolated from a subset of cells after 24 hours of PE treatment and expression level of ANF, a hypertrophic marker gene. was assessed by qRT-PCR (FIG. 2C). N≥6. *P≤0.05.
Figure 2B:
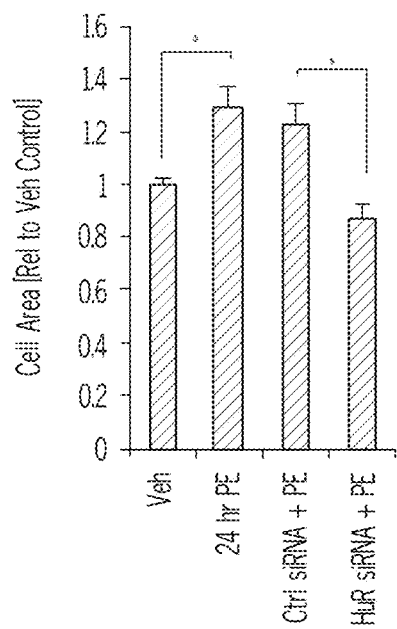
Figure 2C:
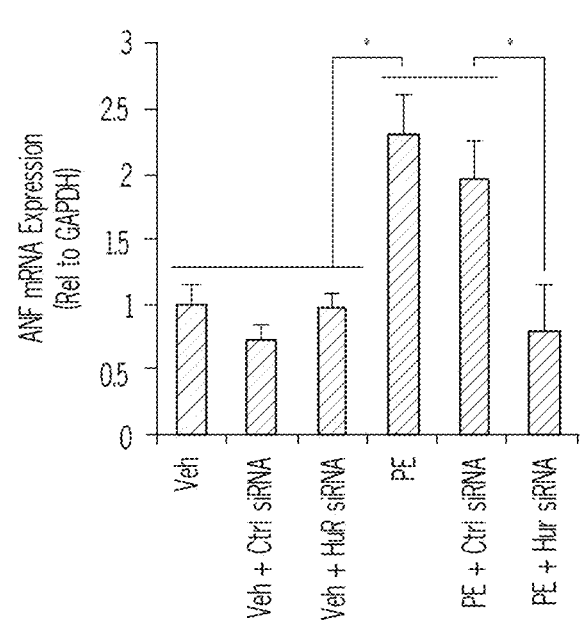

HuR Knockdown or Pharmacological Inhibition Reduces Cardiomyocyte Hypertrophic Growth:

To determine if HuR is necessary for PE-mediated NRVM hypertrophy, expression of HuR protein was knocked down via transient transfection with HuR siRNA (FIG. 2A; top panel). Results show that while transfection of nontargeting control siRNA had no effect on hypertrophic cell growth, HuR knockdown significantly reduced the PE-mediated increase in cell area as determined via WGA staining (1.23±0.07-fold increase in cell size in non-targeting control siRNA+PE treated cells vs. 0.87±0.05-fold in HuR siRNA+ PE-treated cells; P<0.01) (FIG. 2A; bottom panel and FIG. 2B). Furthermore, we show that the PE-induced increase in expression of ANF, a common gene marker of cardiac myocyte hypertrophic growth, is completely inhibited by HuR knockdown (1.95±0.3 fold-induction in control siRNA+PE treated cells vs. 0.80±0.35 fold-induction in HuR siRNA+PE-treated cells; $P \leq 0.05$) (FIG. 2C).

Figure 3A:
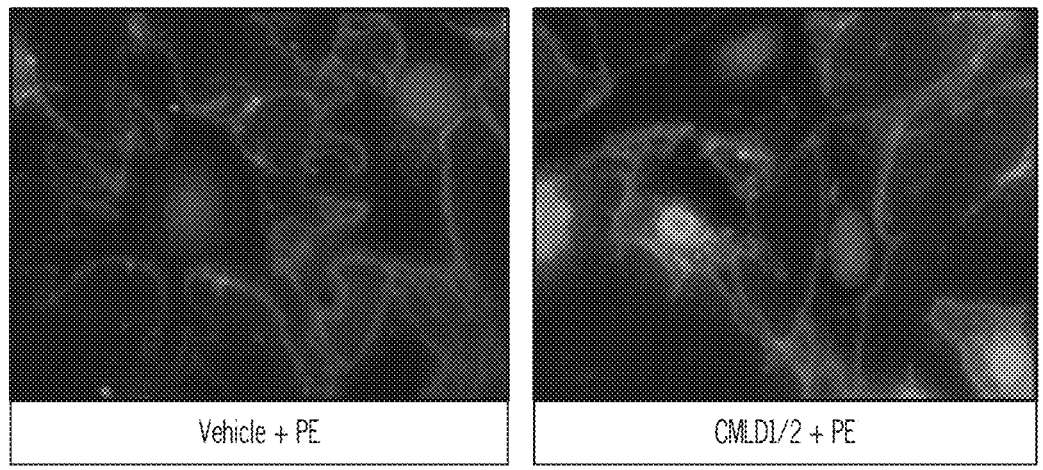
FIG. 3A-C. Pharmacological inhibition of HuR reduces hypertrophic cell growth and ANF expression. NRVMs were treated simultaneously with PE and CMLD-1 and CMLD-2, two small molecule inhibitors of HuR-mRNA interaction. Hypertrophic growth was assessed 24 hours later via WGA staining (FIG. 3A). Cell surface area was quantitatively determined using NIH Image J (FIG. 3B). N=-6 for each group (each N represents the average measurement of 10 cells per well). *P≤0.05. Total RNA was also isolated from a subset of cells and expression level of ANF was assessed by qRT-PCR (FIG. 3C). *P≤0.05.
Figure 3B:
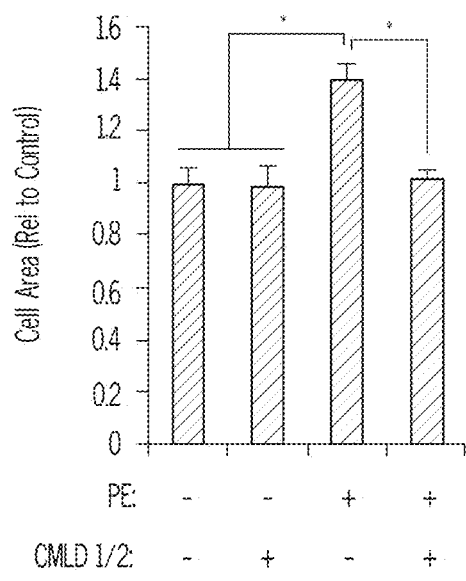
Figure 3C:
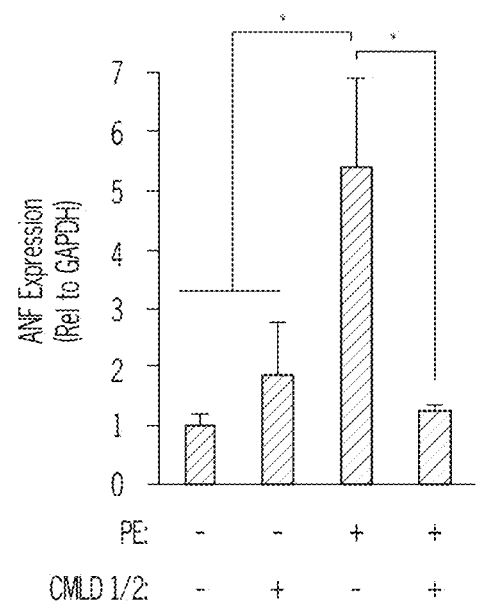

We also show that a similar reduction in PE-induced hypertrophic growth can be achieved via pharmacological inhibition of HuR using newly developed small-molecule inhibitors of HuR (CMLD-1 and CMLD-2) that act through disruption of HuR binding to target mRNA (X. Wu, L. Lan, D. M. Wilson, R. T. Marquez, W.-C. Tsao, P. Gao, et al., Identification and Validation of Novel Small Molecule Disruptors of HuR-mRNA Interaction, ACS Chem. Biol. (2015) 150317154550000-9. doi:10.1021/cb500851u, the entire disclosure of which is incorporated herein by this citation). Simultaneous treatment with the HuR inhibitors CMLD-1 and CMLD2- (both at their respective IC50 values) significantly inhibits the increase in PE-induced cell size (1.39±0.07-fold increase in cell size in vehicle+PE treated cells vs. 1.02±0.03-fold in CMLD1/2+PE-treated cells; P<0.01) (FIG. 3A; bottom panel and FIG. 3B). Similar to iRNAmediated knockdown of HuR, we also show that pharmacological inhibition of HuR reduces PE-induced ANF expression (5.4±1.4 fold-induction in vehicle+PE treated cells vs. 1.3±0.1 fold-induction in CMLD1/2+PE-treated cells; P<0.05) (FIG. 3C). These results indicate that HuR is necessary for PE-induced NRVM hypertrophy.

Figure 4A:
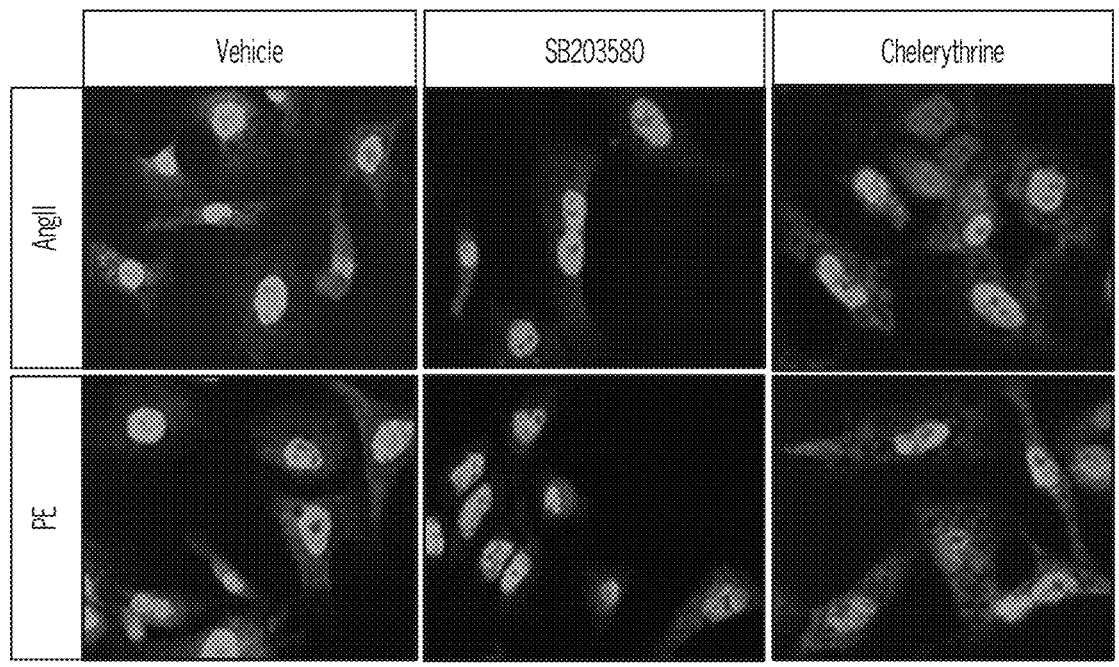
FIG. 4A-B. Nucleo-cytoplasmic shuttling of HuR downstream of AngII and PE is dependent on p38 MAPK, but not PKC. NRVMs treated with AngII (100 nM) or PE (10 µM) show significant cytoplasmic translocation of HuR vs. control (vehicle) cells as measured by IHC 15 minutes after treatment. Treatment with the p38 inhibitor SB203580 shows that this translocation is dependent on p38 MAPK, but treatment with the PKC inhibitor chelerythrine does not affect HuR translocation in myocytes (FIG. 4A). HuR translocation was quantified as the ratio of cytoplasmic to nuclear cell fluorescent intensity (FIG. 4B). N≥5 for each group (each N represents the average measurement of 10 cells per well). *P≤0.05.
Figure 4B:
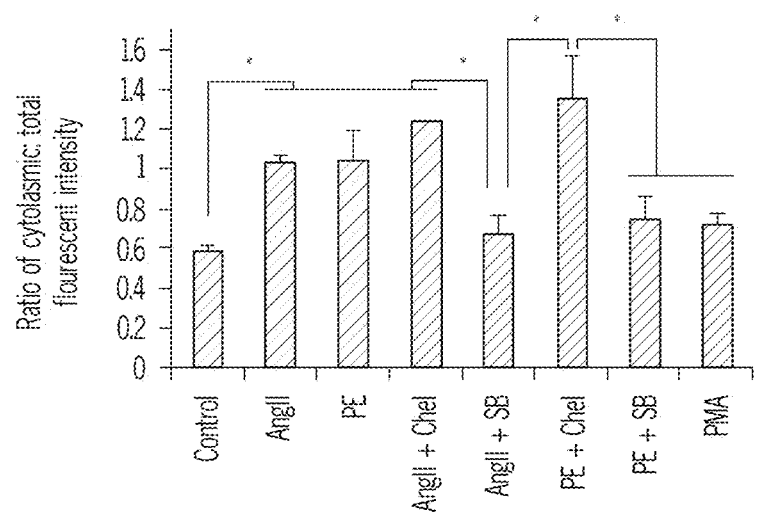

HuR Translocation Downstream of Gαq-Coupled Receptors is Dependent on p38 MAPK, but not Canonical Gq-PKC Signaling:

PE induces myocyte hypertrophy downstream of Gαq-coupled α1-adrenergic receptors (α1-ARs), and the heterotrimeric Gq proteins have long been known to be necessary and sufficient for the development of pathological cardiac hypertrophy (J. W. Adams, J. H. Brown, *G-proteins in growth and apoptosis: lessons from the heart*, Oncogene. 20 (2001) 1626-1634. doi:10.1038/sj.onc.1204275, the entire disclosure of which is incorporated herein by this citation). Thus, to determine if the signaling pathways by which HuR is activated in cardiac myocytes are downstream of Gαq, we treated NRVMs with agonists of two independent Gαq-coupled receptors: PE (an α1-AR agonist) and AngII (an angiotensin I receptor, AT1, agonist). Indeed, results show a significant cytoplasmic translocation of HuR within 15 minutes after treatment with either PE or AngII (0.71±0.04 in vehicle control vs. 1.05±0.06 in 15 hr PE-treated cells, $P<0.001$ vs. Ctrl and 1.06±0.04 in 15 hr AngII-treated cells, $P<0.001$ vs. Ctrl) (FIG. 4A-B).

It has previously been shown that HuR is activated downstream of p38 MAPK and PKC in other tissue types, and both p38 MAPK and PKC are known to signal downstream of Gq proteins and play a role in pathological hypertrophy (K. Abdelmohsen, A. Lal, H. H. Kim, M. Gorospe, *Posttranscriptional orchestration of an anti-apoptotic program by HuR*, Cell Cycle. 6 (2007) 1288-1292, and G. W. Dorn, T. Force, *Protein kinase cascades in the regulation of cardiac hypertrophy*, J. Clin. Invest. 115 (2005) 527-537. doi:10.1172/JCI2417). Thus, we employed pharmacological inhibition of p38 MAPK and PKC (via SB203580 and chelerythrine, respectively) to determine the role of these kinases in PE/AngII-mediated translocation of HuR prior to myocyte hypertrophy. Our results demonstrate that HuR translocation downstream of both PE and AngII is dependent on p38 MAPK, but not PKC (FIG. 4A-B). SB203580-mediated inhibition of p38 MAPK significantly reduced HuR translocation following treatment with either PE (0.68±0.08, $P<0.001$) or AngII (0.76±0.07, $P<0.01$) compared to PE alone (1.05±0.06). Given that treatment with chelerythrine had no effect on HuR translocation, proper inhibition of PKC was confirmed by showing a reduction of PKC substrate phosphorylation (data not shown). A lack of HuR translocation following application of a direct activator of PKC (PMA, 2 μM) also confirms that PKC activation alone is insufficient to induce HuR translocation in cardiac myocytes (FIG. 4B). These results identify p38 MAPK as an upstream signaling mediator of HuR translocation in hypertrophic cardiac myocytes.

Figure 5A:
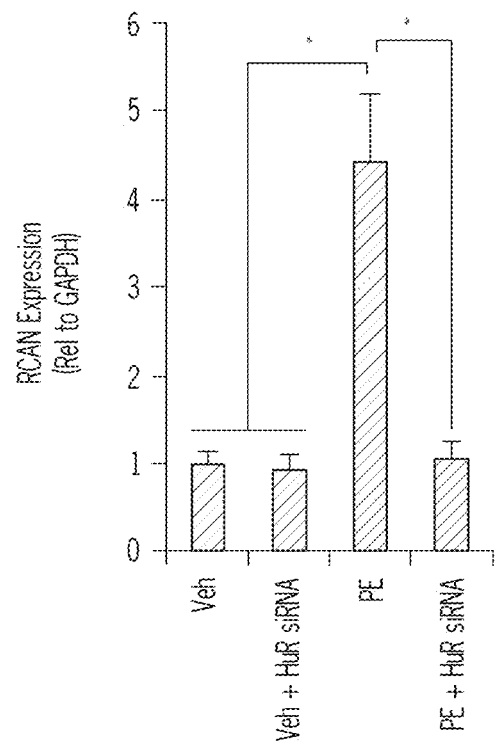
FIG. 5A-B. HuR knockdown or inhibition inhibits NFAT transcriptional activation and downstream gene expression. Expression level of the NFAT-dependent gene RCAN was assessed via qRT-PCR in control or PE-treated NRVMs with and without siRNA mediated HuR knockdown (FIG. 5A). N≥3. *P≤0.05. NFAT transcriptional activation was directly assessed via transient transfection of NRVMs with an NFAT-luciferase reporter. Consistent with other assessed time-points of NRVM hypertrophy. luciferase activity was measured 24 hours following treatment with PE and HuR pharmacological inhibition with small molecule inhibitors of HuR-mRNA interaction (via CMLD-1 and CMLD-2) (FIG. 5B). N≥8. *P≤0.05.

HuR Mediates the Activity of the Pro-Hypertrophic Transcription Factor NFAT:

To begin to decipher the downstream mechanisms by which HuR translocation promotes cardiomyocyte hypertrophy, we assessed the effect of HuR knockdown and inhibition on the transcriptional activity of NFAT, the activation of which is a hallmark of cardiac hypertrophy B. J. Wilkins, Y.-S. Dai, O. F. Bueno, S. A. Parsons, J. Xu, D. M. Plank, et al., *Calcineurin/NFAT coupling participates in pathological, but not physiological, cardiac hypertrophy*, Circ. Res. 94 (2004) 110-118. doi:10.1161/01.RES.0000109415.17511.18, the entire disclosure of which is incorporated herein by this citation). First, we show that the PE-induced expression of the NFAT target gene RCAN1, a commonly used downstream gene marker of NFAT activation, is inhibited following siRNA-mediated knockdown of HuR (4.43±0.77 fold-induction in PE treated cells vs. 1.04±0.19 fold-induction in HuR siRNA+PE-treated cells; $P<0.05$) (FIG. 5A).

Figure 5B:
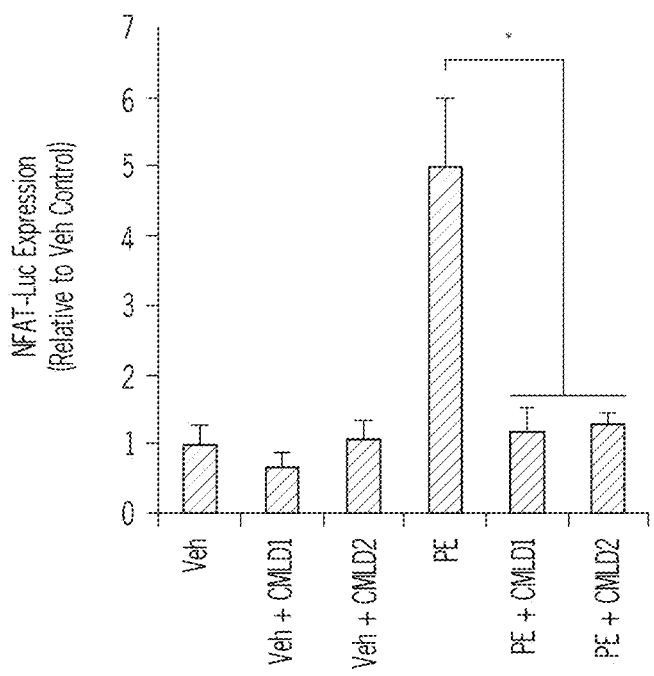

Using a luciferase reporter assay to more directly probe NFAT transcriptional activity, we also show a significant inhibition of NFAT reporter activity after a 24-hour exposure to PE using pharmacological inhibition of HuR (FIG. 5B). Treatment with the HuR inhibitors CMLD-1 or CMLD-2, (each at their determined IC50 values for HuR inhibition of 4.0 μm, 2.4 μm, respectively, (X. Wu, L. Lan, D. M. Wilson, R. T. Marquez, W.-C. Tsao, P. Gao, et al., *Identification and Validation of Novel Small Molecule Disruptors of HuR-mRNA Interaction*, ACS Chem. Biol. (2015) 150317154550000-9. doi:10.1021/cb500851u, the entire disclosure of which is incorporated herein by this citation) has no significant effect on basal NFAT activity. However, when administered simultaneously with PE, CMLD-1 and CMLD-2 completely inhibited the increase in PE-mediated NFAT reporter activity (1.19±0.30-fold vs. vehicle control in PE+CMLD1 treated and 1.30±0.14 in PE+CMLD2 treated compared to 5.02±0.98 in cells treated with PE alone, both are $P<0.001$ vs. PE alone) (FIG. 5B). Taken together with the reduction in NFAT-dependent RCAN expression, these results demonstrate that HuR inhibition prevents transcriptional activation of NFAT.

Figure 6A:
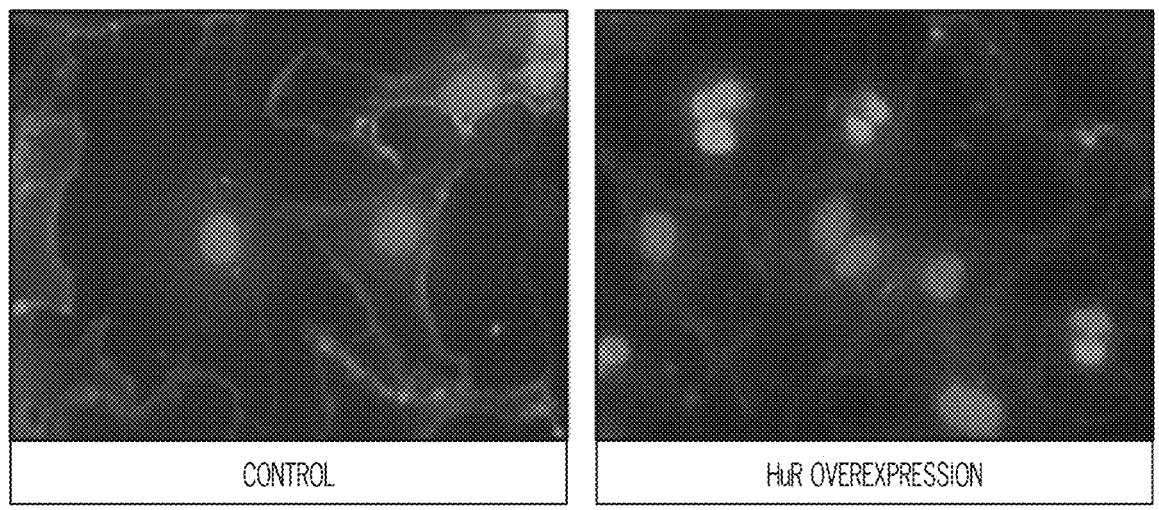
FIG. 6A-C. HuR overexpression is sufficient to induce hypertrophic cell growth and NFAT transcriptional activation. Overexpression of HuR induces hypertrophic cell growth, as observed by an increase in total cell area, compared to treatment with a control plasmid (FIG. 6A). N≥3. *P≤0.05. Cell surface area was quantitatively determined using NIH Image J (FIG. 6B). Overexpression of HUR is sufficient to induce NFAT luciferase reporter expression compared to transfection with a control plasmid (FIG. 6C). N=8. *P≤0.05.
Figure 6B:
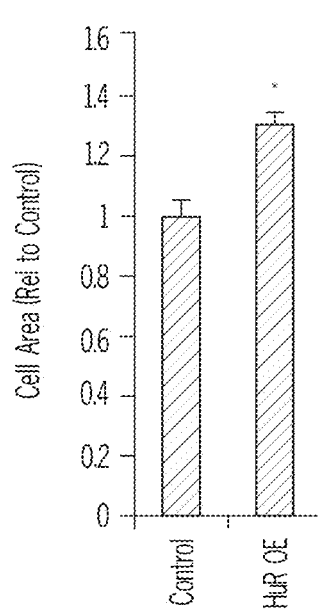
Figure 6C:
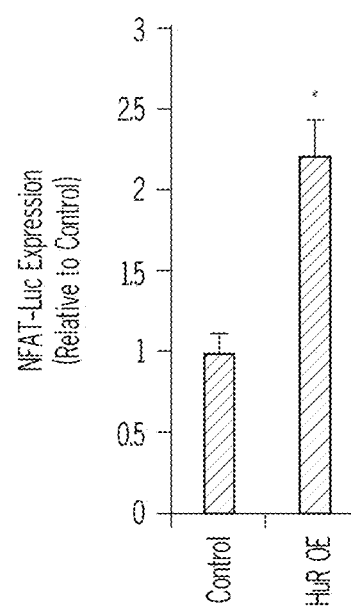
Figure 7A:
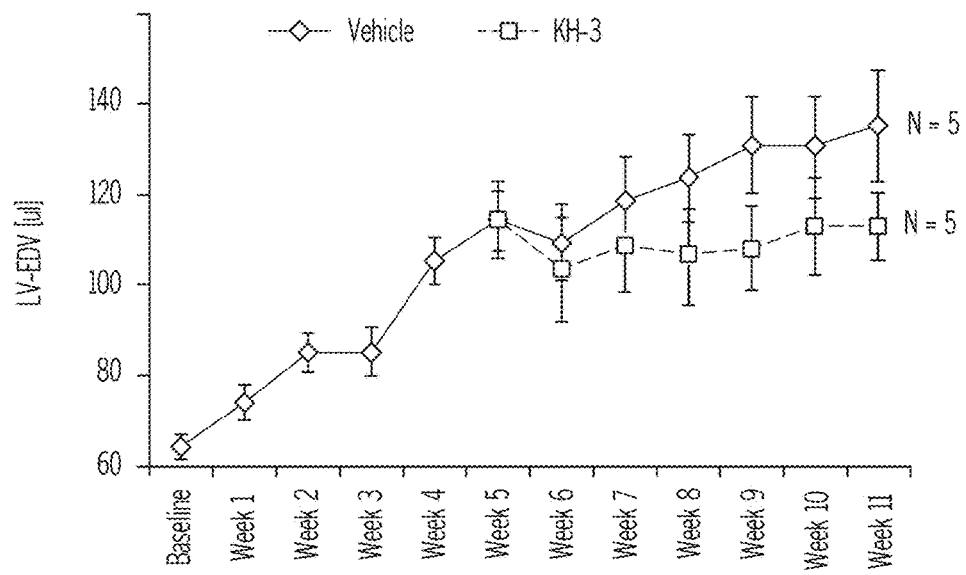
FIG. 7A-C. KH-3 reduces ventricular dilation and improves ejection fraction in a pressure overload (aortic constriction) mouse model of heart failure. Mice (N=10) were subjected to aortic constriction (TAC) to induce cardiac hypertrophy and heart failure. After week 4, they were randomized to receive either KH-3 (50 mg/kg 3×/week) or Vehicle (5 mice to each group). KH-3 is a small molecule inhibitor of HuR-mRNA interaction that is available from. Mice in the KH-3 group showed significantly preserved cardiac structure by preventing further increases in left ventricle end diastolic volume (LV-EDV; A, B) and left ventricle end systolic volume (LV-ESV; B). This result is confirmed by showing that KH-3 also blunts further increases in left ventricle (LV) diameter (FIG. 7C).
Figure 7B:
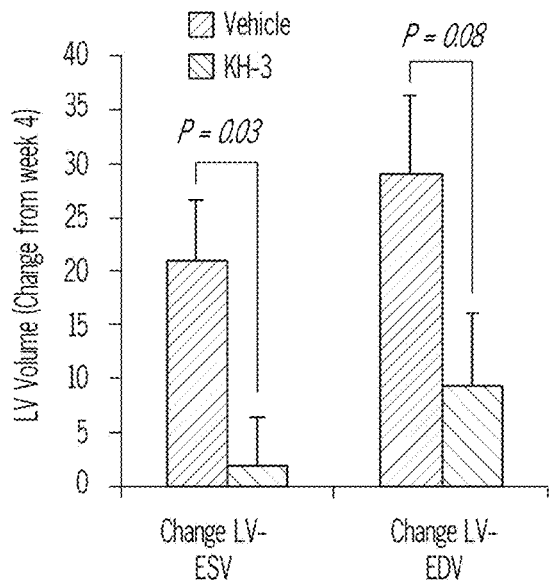
Figure 7C:
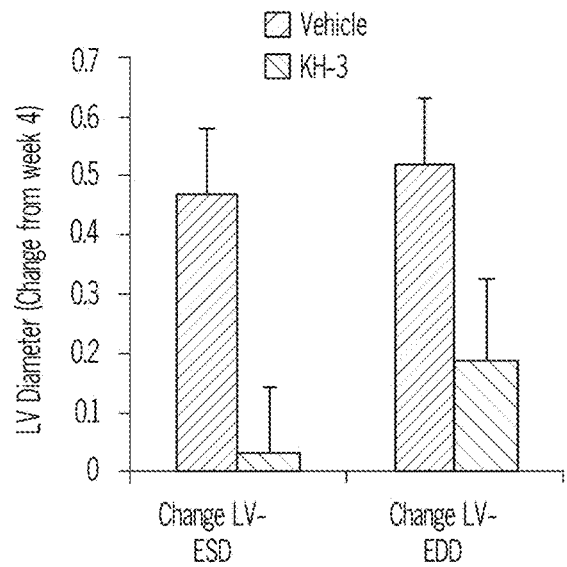
Figure 8A:
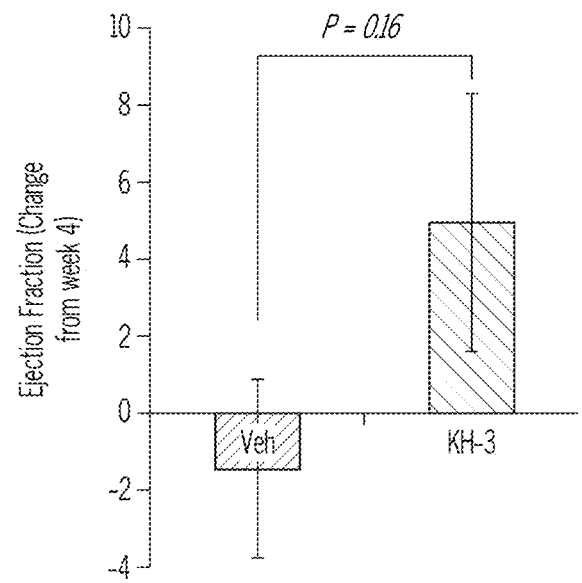
FIG. 8A-C. KH-3 reduces ventricular dilation and improves ejection fraction in a pressure overload (aortic constriction) mouse model of heart failure. Treatment with KH-3, a small molecule inhibitor of HuR-mRNA interaction, shows a strong trend toward improving cardiac function (as measured by ejection fraction; following pressure overload-induced pathological cardiac hypertrophy (FIG. 8A). As expected, there is also a strong trend toward a reduction in cardiac hypertrophy following KH-3 treatment (as measured by either heart weight to body weight (FIG. 8B) or heart weight to tibia length ratio (FIG. 8C)).
Figure 8B:
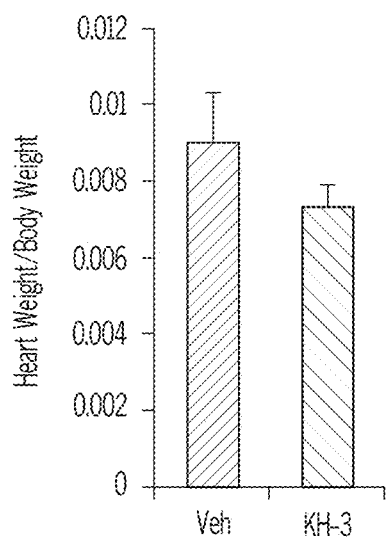
Figure 8C:
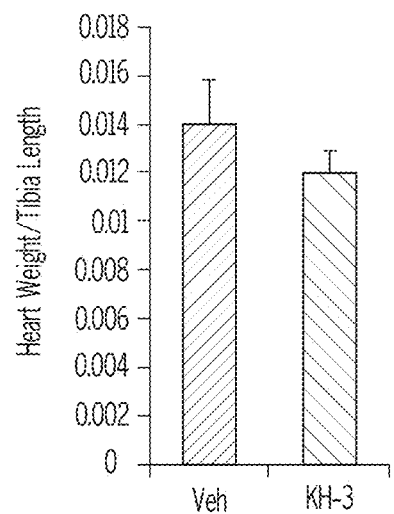

HuR Overexpression is Sufficient to Drive Hypertrophic Cell Growth:

Finally, our results demonstrate that overexpression of HuR resulted in a significant increase in NRVM cell size (1.31±0.03-fold larger than cells treated with a control plasmid, $P<0.001$) (FIG. 6A-B). In addition, overexpression of HuR was found to induce a 2.2-fold increase in NFAT reporter activity compared to control plasmid ($P<0.001$) (FIG. 6C). This suggests that not only is HuR necessary for the development of hypertrophic signaling in cardiac myocytes, but also the overexpression of HuR is sufficient to induce hypertrophic signaling.

Discussion

This work is the first to show that HuR plays a direct role in cardiomyocyte hypertrophy. Not only does HuR knockdown or pharmacological inhibition using CMLD-1, CMLD-2, or a combination thereof prevent myocyte hypertrophy in an established model of phenylephrine-induced NRVM hypertrophy, but HuR overexpression is alone sufficient to induce hypertrophic signaling. To begin to elucidate the mechanisms by which HuR promotes hypertrophy, we also show that cytoplasmic translocation of HuR downstream of two separate Gαq coupled GPCRs (AT1 and α1-AR) is dependent on p38 MAPK but not PKC. In addition, the downstream mechanisms of HuR in cardiomyocyte hypertrophy appear to be mediated through transcriptional activation of the pro-hypertrophic transcription factor NFAT.

Activation of heterotrimeric Gαq (Gq) proteins downstream of Gq-coupled GPCRs such as angiotensin receptors (AT1) or α1-ARs is a known mediator of pathological hypertrophy (J. W. Adams, J. H. Brown, *G-proteins in growth and apoptosis: lessons from the heart*, Oncogene. 20 (2001) 1626-1634. doi:10.1038/sj.onc.1204275, and S. Mishra, H. Ling, M. Grimm, T. Zhang, D. M. Bers, J. H. Brow et al., *Cardiac Hypertrophy and Heart Failure Development Through Gq and CaM Kinase II Signaling*, Journal of Cardiovascular Pharmacology. 56 (2010) 598-603. doi: 10.1097/FJC.0b013e3181e1d263). Furthermore, cardiac specific overexpression of Gq is sufficient to induce cardiac hypertrophy (D. D. D'Angelo, Y. Sakata, J. N. Lorenz, G. P.

Boivin, R. A. Walsh, S. B. Liggett, et al., *Transgenic Galphaq overexpression induces cardiac contractile failure in mice*, Proc. Natl. Acad. Sci. U.S.a. 94 (1997) 8121-8126). Activation of the Gq-protein is observed downstream of nearly every stimulus of pathological hypertrophy, but the specific mechanisms by which its activation results in cardiac hypertrophy have yet to be fully elucidated. Thus, identification of HuR as a key signaling node downstream of Gq activation in the hypertrophic myocyte would represent a significant enhancement in our understanding of Gq-mediated hypertrophy.

Prior work demonstrates that both p38 MAPK and PKC are known to signal downstream of Gq proteins and play a role in pathological cardiac hypertrophy (K. Abdelmohsen et al., *Posttranscriptional orchestration of an anti-apoptotic program by HuR*, Cell Cycle. 6 (2007) 1288-1292 and G. W. Dorn, T. Force, *Protein kinase cascades in the regulation of cardiachypertrophy*, J. Clin. Invest. 115 (2005) 527-537. doi:10.1172/JCI24178). HuR has also been shown to be targeted by both PKC (S158, S221, and S318) and p38 MAPK (T118), with phosphorylation at each of these sites shown to induce HuR translocation and RNA binding activity in other cell types (A. Doller, et al., *Posttranslational modification of the AU-rich element binding protein HuR by protein kinase Cdelta elicits angiotensin II-induced stabilization and nuclear export of cyclooxygenase 2 mRNA*, Mol. Cell. Biol. 28 (2008) 2608-2625. doi:10.1128/MCB.01530-07; A. Doller et al., *High-constitutive HuR phosphorylation at Ser 318 by PKC{delta} propagates tumor relevant functions in colon carcinoma cells*, Carcinogenesis. 32 (2011) 676-685. doi:10.1093/carcin/bgr024; A. Doller et al., *Protein kinase C alpha-dependent phosphorylation of the mRNA-stabilizing factor HuR: implications for posttranscriptional regulation of cyclooxygenase-2*, Mol. Biol. Cell. 18 (2007) 2137-2148. doi:10.1091/mbc.E06-09-0850; V. Lafarga et al., *p38 Mitogen-activated protein kinase-and HuRdependent stabilization of p21(Cip1) mRNA mediates the G(1)/S checkpoint*, Mol. Cell. Biol. 29 (2009) 4341-4351. doi:10.1128/MCB.00210-09; and K. Abdelmohsen, M. Gorospe, *Posttranscriptional regulation of cancer traits by HuR*, Wiley Interdiscip Rev RNA. 1 (2010) 214-229. doi: 10.1002/wrna.4). However, these results are the first to show a functional link between Gq signaling pathways and HuR activation via p38 MAPK in cardiac myocytes. Surprisingly, our data suggests that PKC activity does not mediate acute HuR translocation in cardiac myocytes. This was an unexpected result given prior work showing that PKC modulates HuR translocation downstream of AngII in human mesangial cells (A. Doller, et al., *Posttranslational modification of the A U-rich element binding protein HuR by protein kinase Cdelta elicits angiotensin l-induced stabilization and nuclear export of cyclooxygenase 2 mRNA*, Mol. Cell. Biol. 28 (2008) 2608-2625). Conversely, our results suggest that non-selective inhibition of all PKC isoforms using chelerythrine shows a trend to enhance HuR translocation in myocytes. While our results suggests that PKC does not mediate HuR translocation in cardiac myocytes, it is possible that PKC still plays a role in HuR binding to target mRNA. To this end, Schulz et al showed that the effect of PKC phosphorylation on HuR function is dependent on the specific site of phosphorylation (S. Schulz et al., *Domain-specific phosphomimetic mutation allows dissection of different protein kinase C (PKC) isotype-triggered activities of the RNA binding protein HuR*, Cell. Signal. 25 (2013) 2485-2495. doi:10.1016/j.cellsig.2013.08.003). Specifically, they used phosphor-mimetic mutants to show that only PKC phosphorylation of Ser221 mediates HuR nucleo-cytoplasmic shuttling, while phosphorylation at either Ser158 or Ser318 mediates RNA binding specificity. Future work will be needed to identify the role that specific HuR phosphorylation sites play in myocyte hypertrophy.

Transcriptional activation of NFAT is recognized as a hallmark event in pathological cardiac hypertrophy (B. J. Wilkins et al., *Calcineurin/NFAT coupling participates in pathological, but not physiological, cardiac hypertrophy*, Circ. Res. 94 (2004) 110-118). Our data shows that HuR knockdown using siRNA inhibits expression of the NFAT-dependent gene RCAN, while pharmacological inhibition of HuR with CMLD-1 or CMLD-2 blocks expression of an NFAT-luciferase reporter following phenylephrine. This acute inhibition of NFAT suggests a possible mechanism for reduced hypertrophic signaling following HuR knockdown or inhibition, though a potential direct link between HuR and NFAT remains to be elucidated. Interestingly, HuR overexpression alone is also sufficient to induce NFAT transcriptional activity. One significant aspect of this work is the application of novel pharmacological inhibitors of HuR recently described by Wu et al (FIG. 3A-C and FIG. 5A-B). This is the first application of pharmacological inhibition of HuR in cardiac myocytes, and given the high recent interest in developing a pharmacological inhibitor of HuR for therapeutic use, represents a potential means for long-term translation of these basic science findings for the treatment of cardiac hypertrophy. Importantly, HuR knockdown or inhibition in basal/resting NRVMs appears to have very little effect. We confirmed this by performing RNA-sequencing on NRVMs following HuR-knockdown and found that only 24 total transcripts were changed between control and siRNA-treated cells (data not shown). This is significant in that it suggests that HuR plays only a very minor role in healthy, non-stressed cardiac myocytes and that HuR inhibition in these cells has little effect on cell function and/or gene expression. Thus, we believe that this work introduces HuR as a novel myocytecentric target to manage hypertrophic growth of cardiac myocytes and for the treatment of cardiac hypertrophy.

This work identifies HuR activation downstream of p38 MAPK as a novel mediator of Gq-dependent cardiomyocyte hypertrophy, and suggests modulation of NFAT transcriptional activity as a potential mechanism for HuR-mediated hypertrophy. These results are the first to demonstrate that HuR is necessary and sufficient to induce hypertrophic signaling in cardiac myocytes.

Figure 9A:
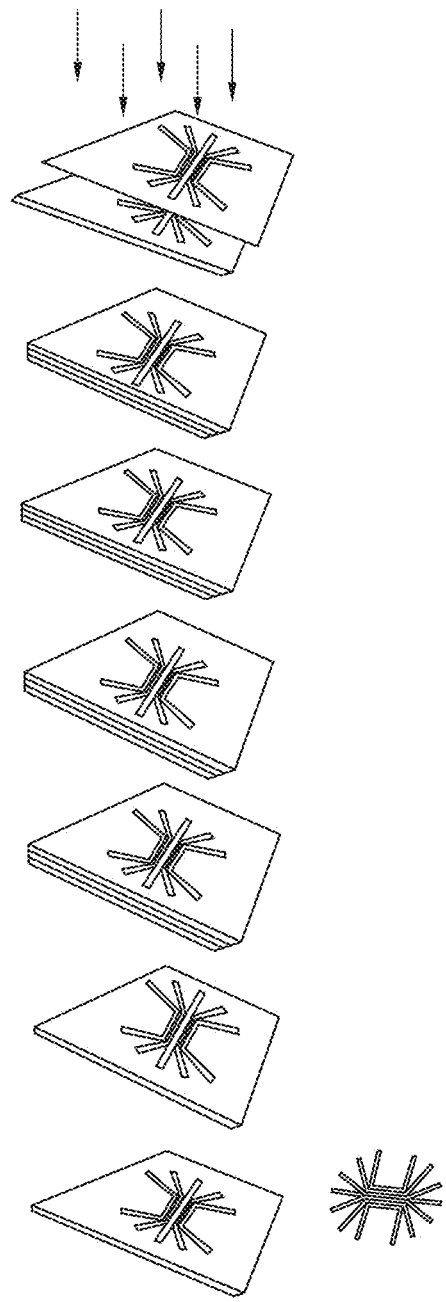
FIG. 9A-B is a schematic illustration depicting the steps for fabricating a microfluidic device and a spot plate containing uniform plasmonic nanoparticle arrays.
Figure 9B:
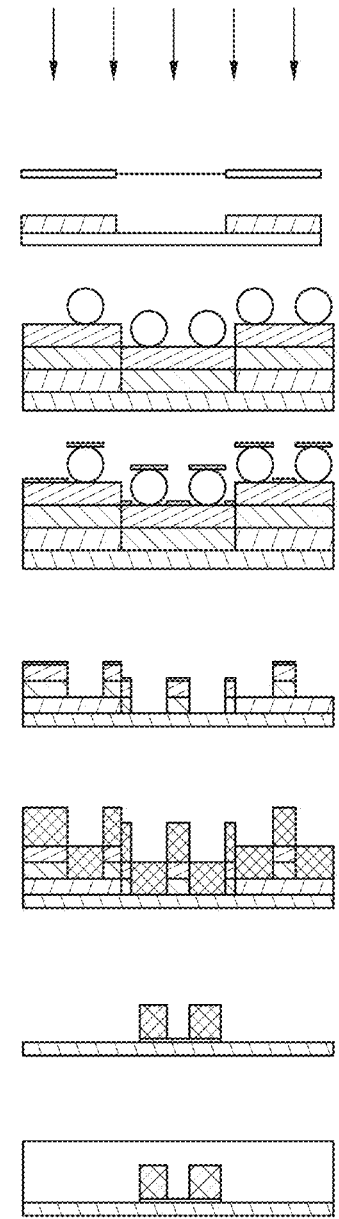

Example 2—Multiplexed Plasomonic-Nanoparticle-Based Assay to Identify Inhibitor of RNA Binding Protein-RNA Interaction Material and Methods Nanoparticle Arrays to be Incorporated into Microfluidic Devices Based on Localized Surface Plasmon Resonance:

As shown schematically in FIG. 9A-B, a pattern for either microfluidic channels or a spot plate is first made on the substrate using photolithography. Next, the hole mask procedure is carried out on top of the patterned photoresist to make the desired nanoparticle array. Briefly, this procedure involves spin coating a layer of poly(methylmethacrylate) (PMMA) followed by a layer of poly(diallyldimethylammonium chloride) (PDDA). Next, polystyrene spheres of a desired size are drop-coated onto the top of the polymer layers and a layer of 5 nm of gold is deposited over the whole assembly. After removal of the polystyrene spheres by tape-stripping, the masks are subjected to oxygen plasma etching to generate holes the same size as the polystyrene spheres. Metals are then deposited into these holes and in the last step, both the PMMA/PDDA polymer mask and the photoresist are removed using acetone, to create nanoparticle arrays in a desired pattern on the substrate. In this specific example, glass was used as a substrate and the glass substrate was bound to similarly patterned PDMS through oxygen plasma etching, creating a chemical, tight seal in the regions that did not contain nanoparticles. The PDMS layer was used to create the channels for the microfluidic devices and to prevent solution migration from spot to spot in the spot plates. This technique is not only scalable and inexpensive, but also allows for the versatile fabrication of nanoparticle arrays ranging from 20 to 400 nm in diameter in any desirable diffraction-limited pattern. In order to demonstrate the utility of this technique, nanoparticle arrays were patterned to generate both 5 and 7-channel microfluidic devices, as well as a 96-well spot plate that was capable of being measured with a standard plate reader in absorption mode. As would be clear to one of ordinary skill in the art, one could extend the principle to pattern a significantly larger number of microfluidic channels or plates containing 384 or even 1536 spots.

Figure 10:
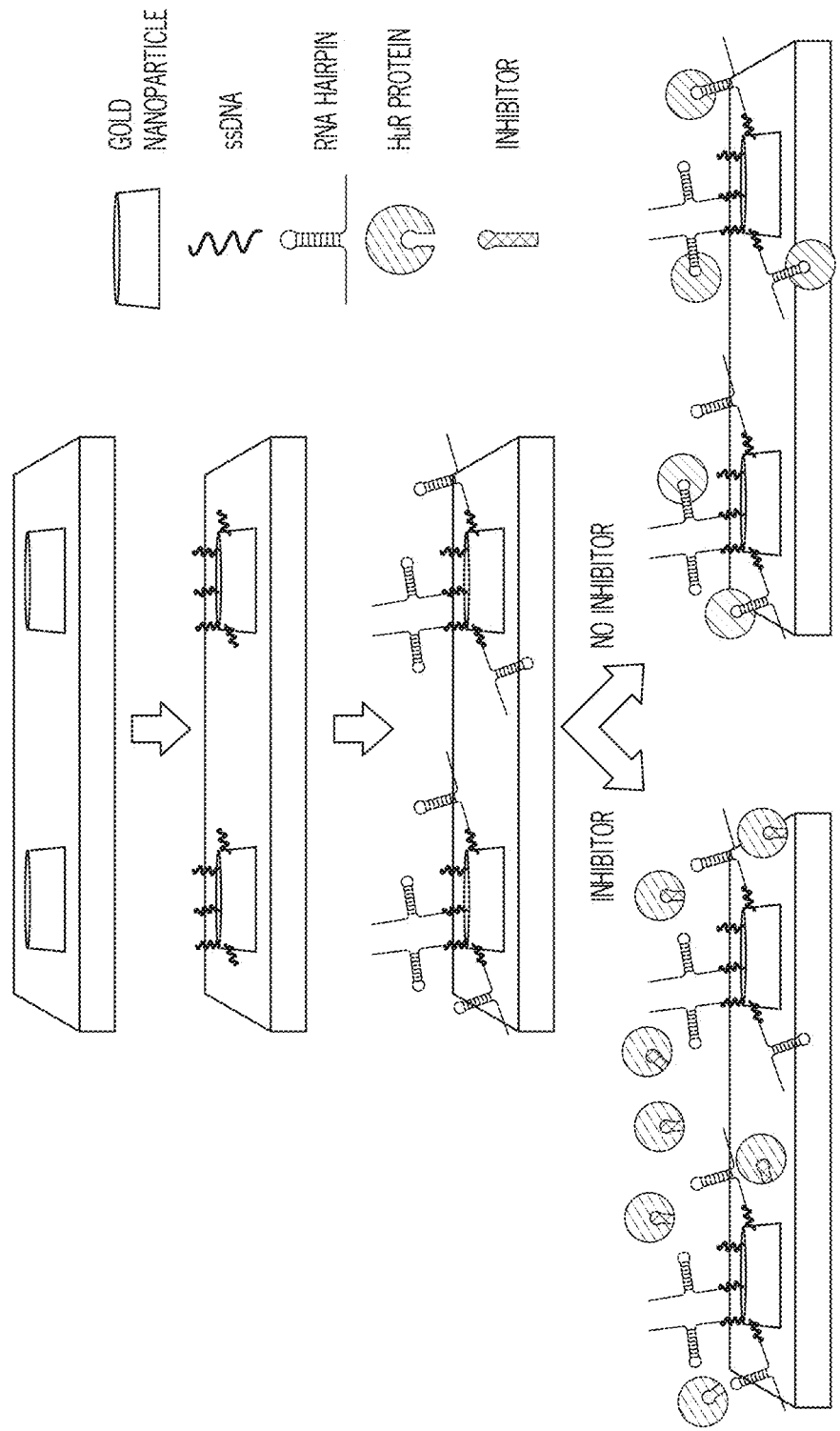
FIG. 10 is a schematic illustration depicting the assay assembly with HuR protein bound (right), and the HuR protein in the presence of a HuR-RNA interaction inhibitor (left). Binding of the HuR to the target RNA and subsequent disruption of this binding by an inhibitor will be readily detected by LSPR shifts.
Figure 11A:
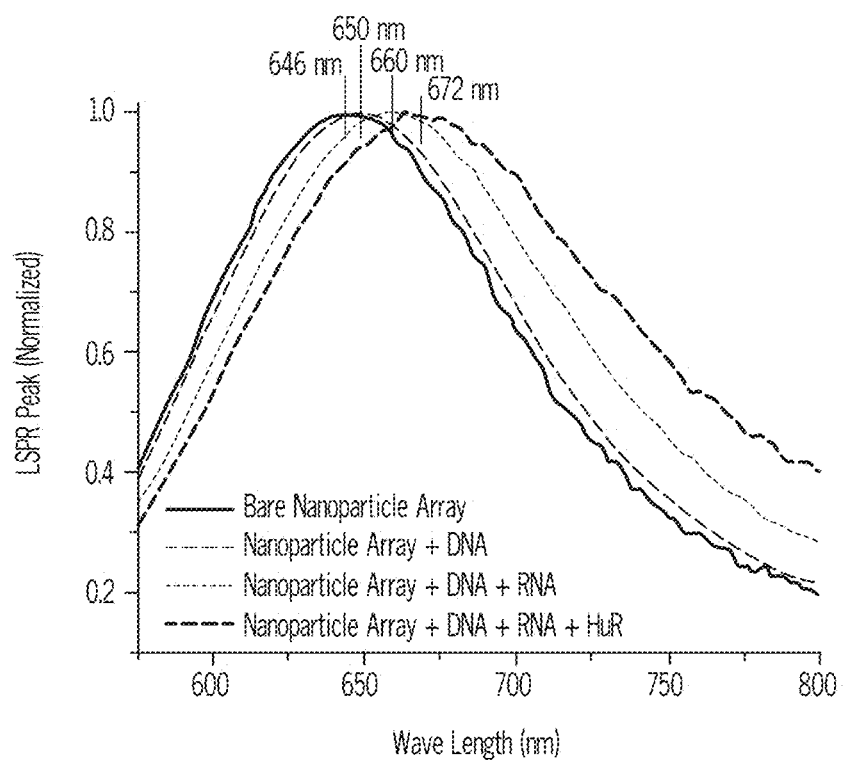
FIG. 11A-C. For Each Step of the Assay Assembly, Sizable LSPR Shifts are Observed Which Allows for Quantitative Measurement of the Expected Binding at Each Step.
Figure 11B:
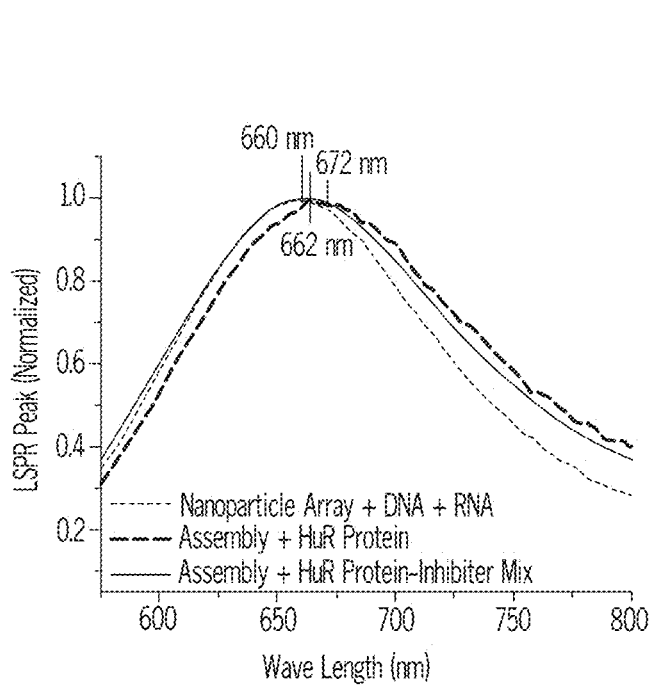
Figure 11C:
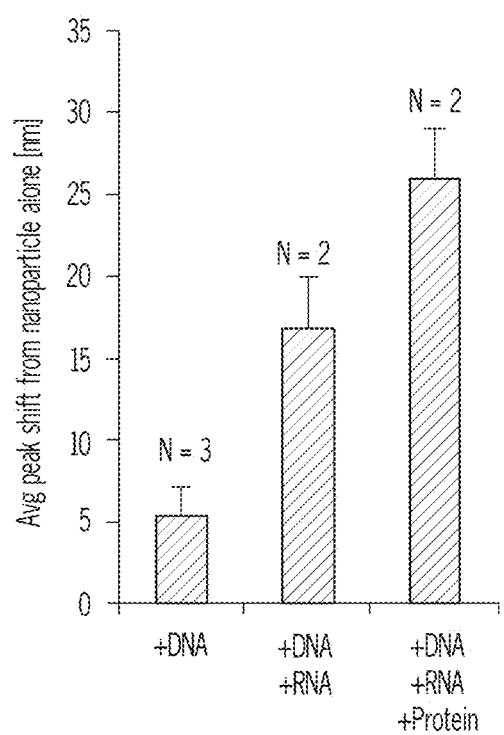

Multiplexed Plasmonic Nanoparticle Assay to Identify Inhibitors of RNA Binding Protein-RNA Interaction:

As shown schematically in FIG. 10, a proof-of-concept study was carried out using gold nanoparticle arrays, 100 nm in diameter and 60 nm in height, were fabricated using Hole Mask Colloidal Lithography as described in herein and as shown in FIG. 9A-B. As shown in FIG. 10, these nanoparticle arrays were first functionalized with single stranded DNA, using thiolated DNA to bind the DNA directly to the gold surface. Next a target RNA strand containing a DNA hybridizing region, which binds via base pair matching with the ssDNA on the nanoparticle, and a hairpin loop containing a HuR target binding site. The specific target RNA strand used (SEQ ID NO 7) contains a specific HuR binding motif, has the RNA sequence 5'-GCG-AAU-UGG-GCC-CGA-CGU-CGC-AUG-GCU-UUU-AUU-UAU-UUU-GCA-UGG-CCG-CGG-GAU-3', and was from Integrated DNA Technologies (IDT). Last, the HuR protein is added and binds to its target site within the RNA hairpin loop. The specific HuR protein used was a recombinant HuR protein from Novus Biologicals (product #:H00001994-P01). For each step of the assembly, sizable LSPR shifts were observed, confirming our ability to quantitatively measure the expected binding at each step (FIG. 11A-C). In addition, as a positive control to demonstrate that we can detect disruption of HuR-RNA binding, we used CMLD-1, HuR-mRNA interaction inhibitor that works through inhibition of RNA binding (FIG. 11C). FIG. 11A demonstrates representative shifts observed with addition of DNA, RNA, and HuR protein to the nanoparticle arrays. FIG. 11B shows the quantitative assessment demonstrating reproducibility of the observed LSPR shifts. FIG. 11C demonstrates that the addition of the HuR inhibitor CMLD-1 resulted in a measurable disruption of HuR-RNA binding as evidenced by the observed leftward shift of 10 nm.

Figure 12:
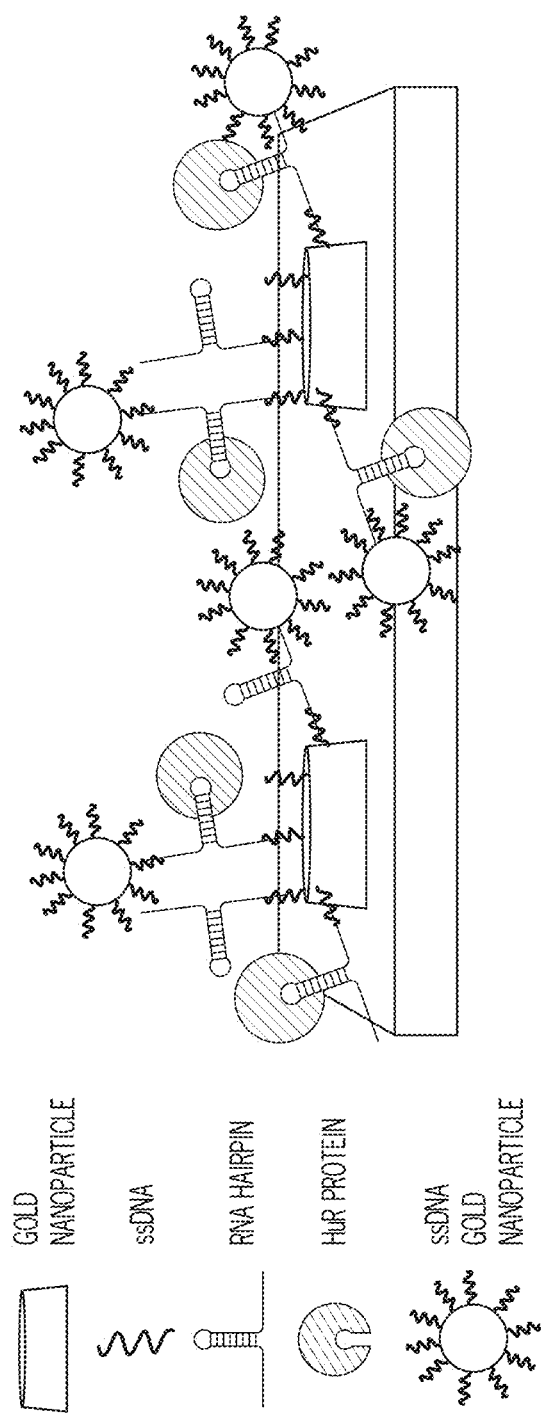
FIG. 12 is a schematic illustration depicting a second nanoparticle assembly can be used to amplify the observed LSPR shifts.

Signal Amplification Via a Second Tethered Nanoparticle:

As shown schematically in FIG. 12, a second nanoparticle assembly can be used to amplify the observed LSPR shifts. The RNA itself will be used to tether a second gold gold nanoparticle to the surface-bound nanoparticle through interactions at both ends with the DNA probe strands.

All documents cited are incorporated herein by reference; the citation of any document is not to be construed as an admission that it is prior art with respect to the present invention.

The invention claimed is:

1. A method of treating cardiac hypertrophy in a subject in need of treatment thereof, the method comprising administering to the subject an effective amount of a small molecule inhibitor of HuR-mRNA interaction selected from the group consisting of CMLD-1, CMLD-2, or a combination thereof.

2. The method of claim 1, wherein the cardiac hypertrophy is associated with heart disease.

3. The method of claim 1, wherein the small molecule inhibitor of HuR-mRNA interaction is administered orally.

4. The method of claim 1, wherein the small molecule inhibitor of HuR-mRNA interaction is administered intravenously.

5. The method of claim 1, wherein the subject is a mammal.

6. The method of claim 1, further comprising administering to the subject one or more additional therapeutic compounds.

7. A method of inhibiting Human antigen R (HuR) in a cardiomyocyte cell, the method comprising contacting the cell with an effective amount of a small molecule inhibitor of HuR-mRNA interaction selected from the group consisting of CMLD-1, CMLD-2, or a combination thereof.

8. The method of claim 7, wherein the cell is mammalian.

* * * * *

UNITED STATES PATENT AND TRADEMARK OFFICE
CERTIFICATE OF CORRECTION

Page 1 of 1

PATENT NO. : 10,933,135 B2
APPLICATION NO. : 16/090705
DATED : March 2, 2021
INVENTOR(S) : Michael Tranter, Sarah Anthony and Samuel Slone It is certified that error appears in the above-identified patent and that said Letters Patent is hereby corrected as shown below:

In the Specification

In Column 3, Line(s) 34, after "gene", delete "." and insert --,--, therefor.

In Column 4, Line(s) 1, after "hypertrophy", delete "." and insert --,--, therefor.

In Column 5, Line(s) 55, delete "Gaq-coupled" and insert --Gαq-coupled--, therefor.

In Column 9, Line(s) 49, delete "for" and insert --of--, therefor.

In Column 9, Line(s) 53, delete "tot" and insert --to--, therefor.

In Column 9, Line(s) 58, after "depending", insert --on--.

In Column 12, Line(s) 50, delete "the a" and insert --the--, therefor.

In Column 22, Line(s) 53, before "candidate", delete "an" and insert --a--, therefor.

In Column 29, Line(s) 1, delete "Gaq-coupled" and insert --Gαq-coupled--, therefor.

In Column 29, Line(s) 4 & 5, delete "Gaq-coupled" and insert --Gαq-coupled--, therefor.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*